United States Patent
Panchal et al.

(10) Patent No.: US 6,309,830 B1
(45) Date of Patent: Oct. 30, 2001

(54) HUMAN SUPPRESSOR TRNA OLIGONUCLEOTIDES AND METHODS OF USE FOR SAME

(75) Inventors: Rekha G. Panchal; Charles J. Link, Jr., both of Des Moines, IA (US)

(73) Assignee: Human Gene Therapy Research Institute, Des Moines, IA (US)

( * ) Notice: Subject to any disclaimer, the term of this patent is extended or adjusted under 35 U.S.C. 154(b) by 0 days.

(21) Appl. No.: 09/229,212

(22) Filed: Jan. 13, 1999

Related U.S. Application Data

(60) Provisional application No. 60/071,416, filed on Jan. 14, 1998.

(51) Int. Cl.⁷ .......................... A61K 48/00; C12N 15/11; C12Q 1/68
(52) U.S. Cl. .............................. 435/6; 435/325; 435/375; 536/23.1; 514/44
(58) Field of Search ........................... 435/6, 320.1, 375, 435/69.1; 514/44; 536/23.2, 23.1

(56) References Cited

U.S. PATENT DOCUMENTS

| | | | |
|---|---|---|---|
| 4,687,737 | 8/1987 | Sharp et al. ........................... | 514/44 |
| 4,970,155 | * 11/1990 | Okasinski ............................. | 435/466 |
| 5,861,501 | * 1/1999 | Benseler et al. .................... | 536/24.5 |

OTHER PUBLICATIONS

Li et al., Ochre Suppressor Transfer RNA restored dystrophin expression in MDX mice, Life Sciences, 61(15): 205–209, 1988.*

Campone JP, "Modulation of the phenotype expression of a human serine tRNA gene by 5'–flanking sequences", *DNA* 7(7) 459–468 (1988).

Temple GF, et al., "Construction of a functional human suppressor tRNA gene: an approach to gene therapy for β–thalassaemia", *Nature*, 296(5857) 537–540 (1982).

O'Neill VA et al., "A human opal suppressor tRNA gene and pseudogene", *Journal of Biological Chemistry*, 260(4) 2501–2508 (1985).

Capone JP et al., "Amber, ochre and opal suppressor tRNA genes derived from a human serine tRNA gene", *EMBO Journal*, 4(1) 213–221 (1985), Eynsham, Oxford GB.

Atkinson J, et al., "Mutations to nonsense codons in human genetic disease: implications for gene therapy by nonsense suppressor tRNAs", *Nucleic Acids Research*, 22(8) 1327–1334 (1994) Oxford GB.

Robinson, et al., "Suppression of single and double non-sense mutations introduced into the diphtheria toxin A–chain gene: a potential binary system for toxin gene therapy", *Human Gene Therapy*, 6:137–143 (1995).

Temple, et al., "Construction of a functional human suppressor tRNA gene: an approach to gene therapy for β–thalassaemia", *Nature*, 337–340 (1982), vol. 296.

Zhang, et al., "Ochre suppressor transfer RNA restorer dystrophin expression in mdx mice", *Life Sciences*, 61(15):205–209 (1998).

Noren, et al., "A general method for site–specific incorporation of unnatural amino acids into proteins", *Science*, 244 182–188 (1989).

Sprinzl, et al., "Compilation of tRNA sequences", *Nucleic Acids Research*, 12 suppl., r1–r57 (IRL Press Limited, Oxford, England) (1984).

Atkinson, et al., "Mutations to nonsense codons in human genetic disease: implications for gene therapy by nonsense suppressor tRNAs", *Nucleic Acids Research*, 22(8) 1327–1334 (1994).

* cited by examiner

Primary Examiner—Robert A. Schwartzman
Assistant Examiner—Janet Epps
(74) Attorney, Agent, or Firm—Zarley, McKee, Thomite, Voorhees & Sease

(57) ABSTRACT

Novel synthetic suppressor tRNA have been provided which provide read-through of internal nonsense mutations, or which can site-specifically alter translation of transcribed sequences. Uses of the same are also provided in genetic engineering protocols including gene therapy treatment of diseases such as Xeroderma pigmentosum.

29 Claims, 10 Drawing Sheets

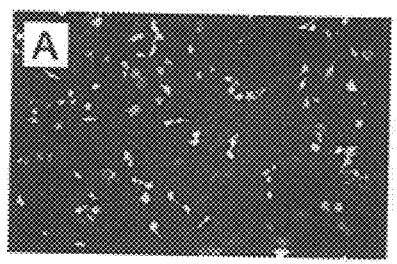
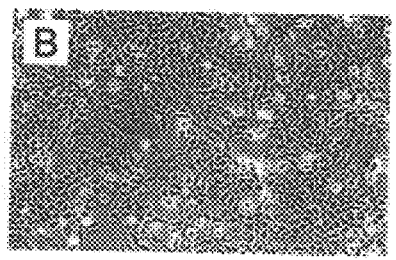
Fig. 3A
Fig. 3B
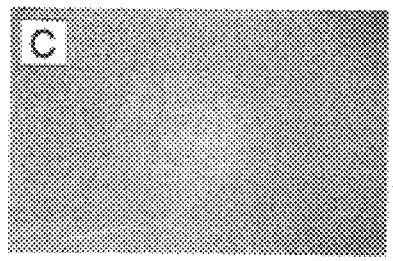
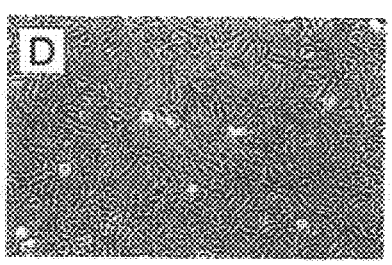
Fig. 3C
Fig. 3D
A.
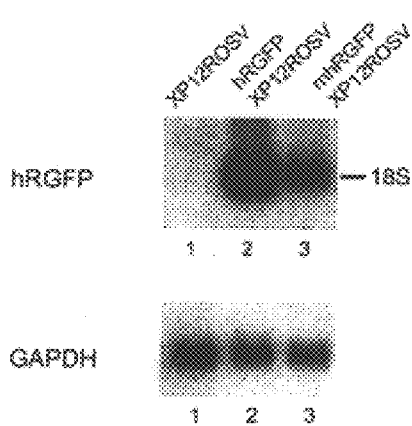
Fig. 4A
B.
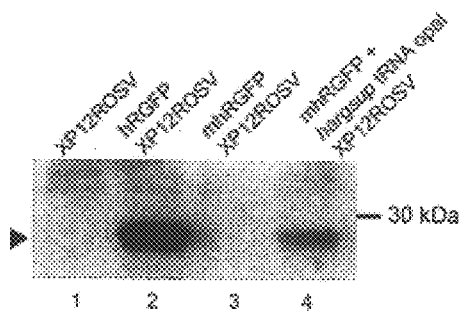
Fig. 4B

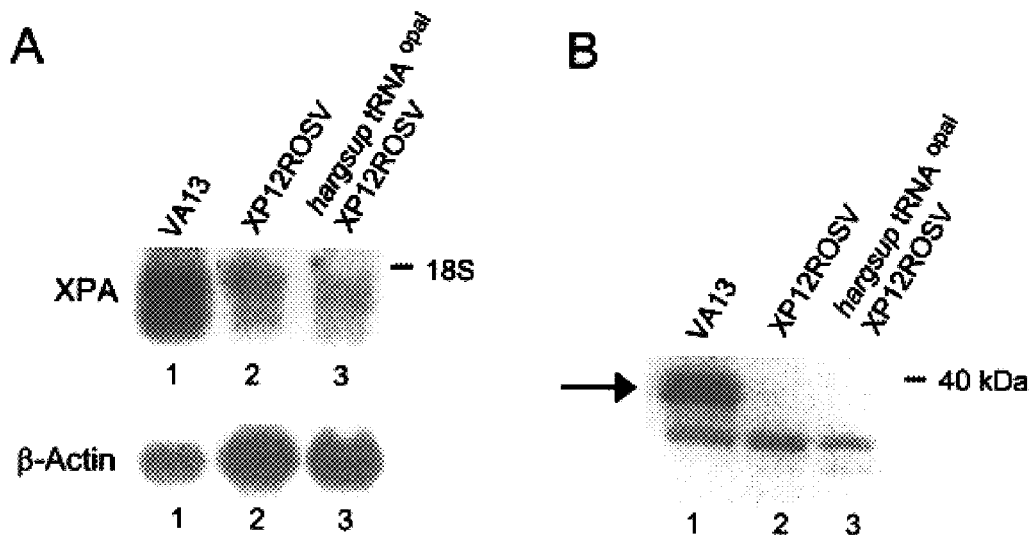
*Fig. 7A*  *Fig. 7B*
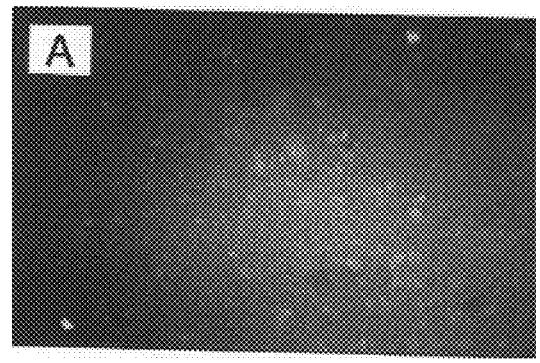
*Fig. 8A*
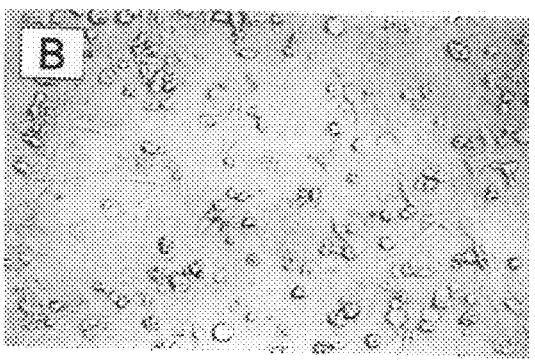
*Fig. 8B*

Human Opal/Amber Suppressor Ser tRNA (del CCA at the 3' end)

pHE 850

Human opal suppressor serine tRNA (using oligos RgP 24/25)

5' gcgcGGTACCAGTAAAAAAGCACGCCGTAGTCGGGAGACCCCAATGATTGAAGTCCATCGCCTTAACCACTCGGCCACGACTACCAGCTGgcgc 3' cgcgCCATGGTCATTTTTTCGTGCGGCATCAGCCCTCTGGGGTTACCTAACTTCAGGTAGCGGAATTGGTGAGCCGGTGCTGATGGTCGACCcgcg
   Kpn I                                                                                    Pvu II

Human amber suppressor serine tRNA (using oligos RgP 18/4)

5' gcgcCTCGAGAGTAAAAAAGCACGCCGTAGTCGGGAGACCCCAATGATTTAGAGTCCATCGCCTTAACCACTCGGCCACGACTACGGTACCgcgc 3' cgcgGAGCTCTCATTTTTTCGTGCGGCATCAGCCCTCTGGGGTTACCTAAATCTCAGGTAGCGGAATTGGTGAGCCGGTGCTGATGCCATGGcgcg
   Xho I                                                                                    Kpn I

Human ochre suppressor serine tRNA (using oligos RgP 73/74)

5' gcgcGCTAGCAGTAAAAAAGCACGCCGTAGTCGGGAGACCCCAATGATTCGAACCTGCGGGAGACCCCAATGATTAAAGTCCATCGCCTTAACCACTCGGCCACGACTACCTCGAGgcgc 3' cgcgCGATCGTCATTTTTTCGTGCGGCATCAGCCCTCTGGGGTTACCTAAATTCAGGTAGCGGAATTGGTGAGCCGGTGCTGATGGAGCTCcgcg
   Nhe I                                                                                    Xho I

Fig. 9

Human Opal/Amber Suppressor Ser tRNA (del CCA at the 3' end)

pHE 850

Human opal suppressor serine tRNA (using oligos RgP24/25)

5' gcgcGGTACCAGTAAAAAAGCACGCCGTAGTCGGCAGGATTCGAACCTGCGCGGGAGACCCCAATGATTTGAAGTCCATGCGCCTTAACCACTCGGCCACGACTACCAGCTGgcgc 3' cgcgCCATGGTCATTTTTTCGTGCGGCATCAGCCGTCCTAAGCTTGGACGCGCCCTCTGGGGTTACCTAAACTTCAGTAGCGGAATTGGTGAGCCGGTGCTGATGGTCGACcgcg
   Kpn I                                                                                                    Pvu II

Human amber suppressor serine tRNA (using oligos 18/4)

5' gcgcCTCGAGAGTAAAAAAGCACGCCGTAGTCGGCAGGATTCGCGCGGGAGACCCCAATGATTAGAGTCCATGCGCCTTAACCACTCGGCCACGACTACGGTACCgcgc 3' cgcgGAGCTCTCATTTTTTCGTGCGGCATCAGCCGTCCTAAGCTTGGACGCGCCCCCTCTGGGGTTACCTAAATCTCAGGTAGCGGAATTGGTGAGCCGGTGCTGATGCCATGGcgcg
   Xho I                                                                                                    Kpn I

Fig. 10

SEQUENCE LISTING

```
<160> NUMBER OF SEQ ID NOS:  16

<210> SEQ ID NO 1
<211> LENGTH: 118
<212> TYPE: DNA
<213> ORGANISM: Artificial Sequence
<220> FEATURE:
<223> OTHER INFORMATION: Description of Artificial Sequence: synthetic

<400> SEQUENCE: 1
gcgcggtacc agtaaaaaaa gcacgccgta gtcggcagga ttcgaacctg cgcggggaga       60
ccccaatgga tttgaagtcc atcgccttaa ccactcggcc acgactacca gctgcgcg       118

<210> SEQ ID NO 2
<211> LENGTH: 119
<212> TYPE: DNA
<213> ORGANISM: Artificial Sequence
<220> FEATURE:
<223> OTHER INFORMATION: Description of Artificial Sequence: synthetic

<400> SEQUENCE: 2
```

```
cgcgccatgg tcattttttt cgtgcggcat cagccgtcct aagcttggac gcgcccctct      60
ggggttacct aaacttcagg tagccggaat tggtgagccg gtgctgatgg tcgaccgcg     119
```

<210> SEQ ID NO 3
<211> LENGTH: 118
<212> TYPE: DNA
<213> ORGANISM: Artificial Sequence
<220> FEATURE:
<223> OTHER INFORMATION: Description of Artificial Sequence: synthetic

<400> SEQUENCE: 3

```
gcgcctcgag agtaaaaaaa gcacgccgta gtcggcagga ttcgaacctg cgcggggaga      60
ccccaatgga tttagagtcc atcgccttaa ccactcggcc acgactacgg taccgcgc      118
```

<210> SEQ ID NO 4
<211> LENGTH: 118
<212> TYPE: DNA
<213> ORGANISM: Artificial Sequence
<220> FEATURE:
<223> OTHER INFORMATION: Description of Artificial Sequence: synthetic

<400> SEQUENCE: 4

```
cgcggagctc tcattttttt cgtgcggcat cagccgtcct aagcttggac gcgcccctct      60
ggggttacct aaatctcagg tagcggaatt ggtgagccgg tgctgatgcc atggcgcg      118
```

<210> SEQ ID NO 5
<211> LENGTH: 118
<212> TYPE: DNA
<213> ORGANISM: Artificial Sequence
<220> FEATURE:
<223> OTHER INFORMATION: Description of Artificial Sequence: synthetic

<400> SEQUENCE: 5

```
gcgcgctagc agtaaaaaaa gcacgccgta gtcggcagga ttcgaacctg cgcggggaga      60
ccccaatgga tttaaagtcc atcgccttaa ccactcggcc acgactacct cgaggcgc      118
```

<210> SEQ ID NO 6
<211> LENGTH: 118
<212> TYPE: DNA
<213> ORGANISM: Artificial Sequence
<220> FEATURE:
<223> OTHER INFORMATION: Description of Artificial Sequence: synthetic

<400> SEQUENCE: 6

```
cgcgcgatcg tcattttttt cgtgcggcat cagccgtcct aagcttggac gcgcccctct      60
ggggttacct aaatttcagg tagcggaatt ggtgagccgg tgctgatgga gctccgcg      118
```

<210> SEQ ID NO 7
<211> LENGTH: 118
<212> TYPE: DNA
<213> ORGANISM: Artificial Sequence
<220> FEATURE:
<223> OTHER INFORMATION: Description of Artificial Sequence: synthetic

<400> SEQUENCE: 7

```
gcgcggtacc agtaaaaaaa gcacgccgta gtcggcagga ttcgaacctg cgcggggaga      60
ccccaatgga tttgaagtcc atcgccttaa ccactcggcc acgactacca gctggcgc      118
```

<210> SEQ ID NO 8
<211> LENGTH: 119
<212> TYPE: DNA

<213> ORGANISM: Artificial Sequence
<220> FEATURE:
<223> OTHER INFORMATION: Description of Artificial Sequence: synthetic

<400> SEQUENCE: 8
cgcgccatgg tcattttttt cgtgcggcat cagccgtcct aagcttggac gcgccctct      60 ggggttacct aaacttcagg tagccggaat tggtgagccg gtgctgatgg tcgaccgcg     119

<210> SEQ ID NO 9
<211> LENGTH: 118
<212> TYPE: DNA
<213> ORGANISM: Artificial Sequence
<220> FEATURE:
<223> OTHER INFORMATION: Description of Artificial Sequence: synthetic

<400> SEQUENCE: 9
gcgcctcgag agtaaaaaaa gcacgccgta gtcggcagga ttcgaacctg cgcggggaga     60
ccccaatgga tttagagtcc atcgccttaa ccactcggcc acgactacgg taccgcgc      118

<210> SEQ ID NO 10
<211> LENGTH: 118
<212> TYPE: DNA
<213> ORGANISM: Artificial Sequence
<220> FEATURE:
<223> OTHER INFORMATION: Description of Artificial Sequence: synthetic

<400> SEQUENCE: 10
cgcggagctc tcattttttt cgtgcggcat cagccgtcct aagcttggac gcgccctct     60 ggggttacct aaatctcagg tagcggaatt ggtgagccgg tgctgatgcc atggcgcg      118

<210> SEQ ID NO 11
<211> LENGTH: 82
<212> TYPE: DNA
<213> ORGANISM: Artificial Sequence
<220> FEATURE:
<223> OTHER INFORMATION: Description of Artificial Sequence: synthetic

<400> SEQUENCE: 11
gtagtcgtgg ccgagtggtt aaggcgatgg actttaaatc cattggggtc tccccgcgca    60
ggttcgaatc ctgccgacta cg                                              82

<210> SEQ ID NO 12
<211> LENGTH: 82
<212> TYPE: DNA
<213> ORGANISM: Artificial Sequence
<220> FEATURE:
<223> OTHER INFORMATION: Description of Artificial Sequence: synthetic

<400> SEQUENCE: 12
gtagtcgtgg ccgagtggtt aaggcgatgg actctaaatc cattggggtc tccccgcgca    60
ggttcgaatc ctgccgacta cg                                              82

<210> SEQ ID NO 13
<211> LENGTH: 82
<212> TYPE: DNA
<213> ORGANISM: Artificial Sequence
<220> FEATURE:
<223> OTHER INFORMATION: Description of Artificial Sequence: synthetic

<400> SEQUENCE: 13
gtagtcgtgg ccgagtggtt aaggcgatgg acttcaaatc cattggggtc tccccgcgca    60
ggttcgaatc ctgccgacta cg                                              82

```
<210> SEQ ID NO 14
<211> LENGTH: 73
<212> TYPE: DNA
<213> ORGANISM: Artificial Sequence
<220> FEATURE:
<223> OTHER INFORMATION: Description of Artificial Sequence: synthetic

<400> SEQUENCE: 14
gaccacgtgg cctaatggat aaggcgtctg acttcagatc agaagattga gggttcgaat      60
cccttcgtgg tta                                                         73

<210> SEQ ID NO 15
<211> LENGTH: 61
<212> TYPE: DNA
<213> ORGANISM: Artificial Sequence
<220> FEATURE:
<223> OTHER INFORMATION: Description of Artificial Sequence:synthetic

<400> SEQUENCE: 15
gcgctcgaga aaacgaaccc cacttaacca cgaagggatt cgaaccctca atcttctgat      60
c                                                                      61

<210> SEQ ID NO 16
<211> LENGTH: 62
<212> TYPE: DNA
<213> ORGANISM: Artificial Sequence
<220> FEATURE:
<223> OTHER INFORMATION: Description of Artificial Sequence:synthetic

<400> SEQUENCE: 16
gcgggtaccg accacgtggc ctaatggata aggcgtctga cttcagatca gaagattgag      60
gg                                                                     62
```

HUMAN SUPPRESSOR TRNA OLIGONUCLEOTIDES AND METHODS OF USE FOR SAME

CROSS-REFERENCE TO A RELATED APPLICATION

This application claims benefit under 35 USC 119(e) of provisional application 60/071, 416 filed Jan. 14, 1998.

BACKGROUND OF THE INVENTION

The four nucleotide bases of DNA molecules carry genetic information. This information, in the form of codons of three contiguous bases is transcribed by mRNA and translated by tRNA and ribosomes to form proteins. The genetic code is the relation between a triplet codon and a particular amino acid. Of the sixty-four possible codon triplets which form the genetic code, there are three stop or terminating codons which are known to stop protein production at cellular ribosomes; the other sixty-one triplets in the code correspond to one or another amino acid. See Table 1

TABLE 1

| UUU Phe | UCU Ser | UAU Tyr | UGU Cys |
|---|---|---|---|
| UUC Phe | UCC Ser | UAC Tyr | UGC Cys |
| UUA Leu | UCA Ser | UAA Stop | UGA Stop |
| UUG Leu | UCG Ser | UAG Stop | UGG Trp |
| CUU Leu | CCU Pro | CAU His | CGU Arg |
| CUC Leu | CCC Pro | CAC His | CGC Arg |
| CAU Leu | CCA Pro | CAA Gln | CGA Arg |
| CUG Leu | CCG Pro | CAG Gln | CGG Arg |
| AUU Lle | ACU Thr | AAU Asn | AGU Ser |
| AUC Lle | ACC Thr | AAC Asn | AGC Ser |
| AUA Lle | ACA Thr | AAA Lys | AGA Arg |
| AUG Met | ACG Thr | AAG Lys | AGG Arg |
| GUU Val | GCU Ala | GAU Asp | GGU Gly |
| GUC Val | GCC Ala | GAC Asp | GGC Gly |
| GUA Val | GCA Ala | GAA Glu | GGA Gly |
| GUG Val | GCG Ala | GAG Glu | GGG Gly |

When genetic instructions are translated at ribosomes, the amino acids are strung together to form complex polypeptides. However, when a stop codon is read, it is interpreted as a stop signal terminating the protein production. The three stop codons are UAG (amber), UAA (ochre) and UGA (opal). Mutations that change a codon to stop codon are called nonsense mutations and, as a result, genetic phenotypes may not be expressed. Thus, despite the presence of a gene directing expression, a crucial protein may not be produced because an unwanted stop signal reaches a ribosome and terminates an unfinished protein.

Transfer RNAs (tRNAs) translate mRNA into a protein on the ribosome. Each transfer RNA contains an anti-codon region that hybridizes with mRNA, and an amino acid which may be attached to the growing peptide. The structural gene of tRNA is about 72–90 nucleotides long and folds into a cloverleaf structure. tRNAs are transcribed by RNA polymerase III and contain their own intragenic split promoters that become a part of the mature tRNA coding sequence (Sharp S. J., Schaack J., Coolen L., Burke D. J. and Soll D., "Structure and transcription of eukaryotic tRNA genes", *Crit. Rev. Biochem,* 19:107–144 (1985); Geiduschek E. O., and Tocchini-Valentini, "Transcription by RNA polymerase III, *Annu. Rev. Biochem.* 57:873–914 (1988)).

Nonsense suppressors are alleles of tRNA genes that are altered in the anticodon so that they can insert an amino acid in response to a termination codon. For example, an ochre mutation results in the creation of a UAA codon in messenger RNA. An ochre suppressor gene produces tRNA with a AUU anticodon that inserts an amino acid at the UAA site permitting continued translation despite the presence of a nonsense codon.

A number of nonsense suppressor tRNA alleles have been identified in prokaryotes and eukaryotes such as yeast and C.elegans. However to date, no mammalian cell line containing functional suppressor tRNA has been isolated using classical genetic selection. Attempts to isolate suppressor tRNAs from higher eukaryotes resulted in the identification of an opal suppressor phosphoserine tRNA in the chicken genome (Hatfield D. L., Dudock B. S., and Eden F. C., "Characterization and nucleotide sequence of a chicken gene encoding an opal suppressor tRNA and its flanking DNA segments", *Proc. Natl. Acad. Sci. U.S.A.,* 80:4940–4944 (1983)), and later in the human genome (O'Neill V. A., Eden F. C., Pratt K., and Hatfield D. L., "A human opal suppressor tRNA gene and pseudogene", *J. Biol. Chem.* 260:2501–2508 (1985)). The two differ from each other at only a single nucleotide position. Suppressor tRNAs may also cause readthrough of the naturally occurring stop codons, thereby producing extended proteins with altered functions. Suppression of termination may be deleterious to the cell, although multiple natural stop codons at the end of the gene may provide safeguard from such harmful effects. The different suppressor tRNAs vary in their suppression efficiency. In *E.coli* and other systems the amber suppressors are relatively more efficient, ochre suppressors are less efficient while opal are the least, this suggests that the amber codons are used infrequently to terminate protein synthesis, while ochre and opal codons are more frequently used as natural termination signals.

Restoration of a normal phenotype by suppressors will depend on the type of amino acid inserted at the position of the nonsense codon. The inserted amino acid may be incompatible with the structure, function or stability of the gene product. Hence, there exists a need for a wide variety of suppressor tRNAs to insert different amino acids. Amber and ochre suppressors derived from a *Xenopus Laevis* tyrosine tRNA gene were shown to be functional in mammalian cells in transient transfection assays as well as in permanent cell lines (Laski F. A., Belagaje U. L., RajBhandary U. L. and Sharp P. A., "An amber suppressor tRNA gene derived by site-directed mutagenesis: cloning and expression in mammalian cells", *Proc. Natl. Acad. Sci. USA,* 79:5813–5817 (1982); Laski F. A., Belagaje R., Hudzoal R. M., Capecchi M. R., Palese P., RajBhandary U. L. and Sharp P. A., "Synthesis of an ochre suppressor tRNA gene and expression in mammalian cells", *EMBO J* 3:2445–2452 (1984); Hudziak R. M., Laski R. A., RajBhandary U., Sharp, P. A. and Capecchi M. R., "Establishment of mammalian cell lines containing multiple nonsense mutations and functional suppressor transfer RNA genes", *Cell* 31:131–146 (1982)). Capone and co-workers similarly generated amber, ochre and opal suppressor tRNA genes derived from a human serine tRNA gene Capone J. P., Sharp P. A. and RajBhandary U. L., "Amber, ochre and opal suppressor tRNA genes derived from a human serine tRNA gene", *EMBO J* 4:213–221 (1985)).

In addition to permitting read-through of a mutation which causes a nonsense codon in the middle of a transcribed protein sequence, there are also times when one wants to manipulate a translation to truncate gene products. In either case, there exists a need for a suppression mechanism which would permit the cellular ribosomes to 'read through' such stop signals when they are unwanted. There is also a need for the opportunity to site specifically modify protein synthesis by deliberately altering the translation of the genetic code to learn about protein function.

It is an object of the present invention to provide novel nonsense suppressor tRNA's which are functional in cells and methods of use of the same in genetic engineering protocols.

SUMMARY OF THE INVENTION

According to the present invention novel oligonucleotide sequences which encode suppressor tRNAs or functional equivalents thereto are provided which, when introduced to cells containing a nonsense mutation, can suppress the expression of the nonsense stop codon allowing for complete translation of protein products. Based upon the knowledge of known human tRNA sequences, synthetic oligonucleotides relating to opal, amber, or ochre mutations are constructed which then may be used in any of a number of genetic engineering protocols.

Briefly, an oligonucleotide is synthesized which comprises the structural component of a known tRNA gene. The sequence of this oligonucleotide is designed based upon the known sequence with substitutions made in the anticodon region of the tRNA causing the specific tRNA to recognize a nonsense or any other specific or desired mutation. For example as shown in FIG. 2 and according to the invention, the sequence of human serine tRNA having an anticodon of TCG was modified to include a substitution of TCA the complement of the opal mutation to cause the tRNA to recognize the opal stop codon rather than the traditional serine codon.

Importantly the sequences for the oligonucleotides of the invention contain only the structural sequence encoding the tRNA molecule as well as a small portion (around 20 nt) of the 3' flanking region. The 5' region is omitted to result in an oligonucleotide that is small and easier to handle (i.e., around 100 nucleotides long). The oligonucleotide sequence comprises the structural component of the gene and includes around 15 bases from the 3' flanking region and none of the 5' noncoding region. Traditional methods using suppressor tRNAs to date have used entire suppressor tRNA encoding molecules which are isolated, cloned and then site-mutated to create the suppressor tRNA. The present invention provides a much simpler method of designing suppressor tRNA encoding oligonucloetides, namely designing a oligonucleotide sequence comprising the structural sequences encoding the tRNA and a portion of the 3' flanking region only. This small oligonucleotide may then be synthetically synthesized, rather than isolated, using standard genetic engineering techniques and these synthetic suppressor tRNAs can be used according to the methods of the invention.

The synthetic suppressor tRNAs and the sequences encoding them or functional equivalents thereof can be used for any of a number of genetic engineering protocols. In a preferred embodiment, these synthetic suppressor encoding tRNAs are introduced into a cell in a gene therapy protocol whether in vitro, ex vivo, or in vivo to suppress the effects of mutations which result in truncated and inactive gene products responsible for disease. The suppressor tRNA encoding oligonucleotides can be directly introduced to cells. They are so similar to native tRNAs that they will be unlikely to generate significant immune response. Additionally and in a preferred embodiment for increased delivery of suppressor encoding tRNAs the tRNA synthetic oligonucleotide sequence may be contained within an appropriate expression vehicle comprising a nucleotide vector.

The term "functional equivalent" as used herein refers to any derivative which is functionally substantially similar to the referenced sequence or protein. In particular the term "functional equivalent" includes derivatives in which nucleotide base(s) and/or amino acid(s) have been added, deleted or replaced without a significantly adverse effect on biological function and which will hybridize under high conditions of stringency according to protocols known in the art and disclosed in Maniantis et. al., "Molecular Cloning" cold Spring Harbor Press, (1989).

DESCRIPTION OF THE FIGURES

In FIG. 1A a normal mRNA with a tyrosine codon is translated into a normal protein. In FIG. 1B, a mutant mRNA with an ochre nonsense mutation is translated to give a truncated protein. In FIG. 1C a nonsense (ochre) suppressor tRNA is provided which allows for translation of the normal protein from the mutant mRNA or "read-through" of the ochre mutation.

FIG. 2(A) Human Arginine tRNA: The sequence (noncoding strand) and the clover leaf structure of the human arginine tRNA is shown (SEQ ID NO:14). A single base change (shown with *) in the anticodon is required to convert the human arginine tRNA into an opal suppressor tRNA. FIG. 2(B) HSV amplicon vector: Amp$^r$, ampicillin resistant; "a", HSV-packaging signal; HSV-tk promoter, HSV-1 thymidine kinase promoter; EBNA-1 modified EBV nuclear antigen gene; ori P, EBV unique latent replication origin; ori S, HSV-1 replication origin.

FIGS. 3A–3D are a figures depicting the restoration of GFP fluorescence using hargsup tRNA$^{Opal}$. (A) GFP fluorescence detected in XP12ROSV cells cotransfected with the mhRGFP expression construct and the pHEhargsup tRNA$^{Opal}$ plasmid. Note bright green fluorescence in multiple cells observed by fluorescence microscopy using a FITC filter. (B) Phase contrast of the same field of transfected XP12ROSV cells as in A. (C) XP12ROSV cells transfected with the mhRGFP vector alone. No significant fluorescence is observed when the nonsense codon is not suppressed. (D) Phase contrast of the same field as in (C).

FIGS. 4A and 4B are figures depicting Northern and Western analysis of hRGFP expression. (A) Northern analysis. Total RNA (10 µg/lane) from XP12ROSV cells (Lane 1) or XP cells transfected with hRGFP gene (lane 2) or with mhRGFP gene containing an opal nonsense mutation (CGC to TGA) at amino acid 73 (lane 3) and probed for hRGFP cDNA (Top panel). GFP transcripts of similar size were obtained. Positions of 18S rRNA is shown. The same blot was then reprobed with Glyceraldehyde-Phosphate Dehydrogenase (GAPDH) housekeeping gene (bottom panel). After normalization of different RNA samples with the GAPDH gene, we observed one third less abundance of the mhRGFP transcript compared to the hRGFP transcript. (B) Detection of GFP protein by Western analysis. Cell lysates were electrophoresed on a 10–20% SDS-PAGE gradient gel and probed with the anti-GFP antibody. XP12ROSV cells expressing the hRGFP gene lone (Lane 2) or coexpressing mhRGFP and hargsup tRNA$^{Opal}$ (Lane 4) showed a full-length 27 kDa GFP protein. Reduced levels of the full-length GFP protein was observed in cells transfected with the mhRGFP and hargsup tRNA$^{Opal}$ plasmids. No full-length GFP protein was detectable in cells expressing the mhRGFP gene in the absence of suppressor tRNA (Lane 3). Nontransfected XP12ROSV cells showed no non-specific staining (Lane 1).

FIGS. 7A and 7B are Northern and Western analysis of XPAC gene expression. (A) Expression of XPAC transcript. Northern analysis of total RNA (10 μg/lane) from normal control VA13 cells (Lane 1) and XP12ROSV cells (Lane 2) probed with a truncated XPAC cDNA is shown in the autoradiogram (top panel). The two bands in the VA13 cells (normal controls) are due to alternative polyadenylation (Tanaka, K. et al., "Analysis of a human DNA excision repair gene involved in group A xeroderma pigmentosum and containing a zinc-finger domain", *Nature* 348 73–78 (1990). The XPAC transcript level was considerably reduced in the XP12ROSV cells. The same blot was reproved for the GAPDH gene, to permit relative normalization of the different RNA samples and shown in the bottom panel. (B) Western analysis to detect XPAC proteins. Western analysis of DNA repair proficient VA13 cells (Lane 1), XP12ROSV cells (Lane 2) and XP12ROSV cells expressing the suppressor tRNA (Lane 3) probed with anti-XPAC antibody. The XPAC protein is easily observed in VA13 cells, but is not detected in either XP12ROSV cells alone or XP12ROSV cells transfected with hargsup tRNA$^{Opal}$.

FIGS. 8A and 8B depict the transduction of XP12ROSV cells with pHEhargsup tRNA$^{Opal}$ amplicon vector packaged into HSV-1 virions. (A) GFP fluorescent cells were observed when XP12ROSV cells expressing the mhRGFP gene were transduced with the pHEhargsup tRNA$^{Opal}$ amplicon vector, suggesting a successful in vitro delivery of the suppressor tRNA by the herpesvirus amplicon system and suppression of the nonsense mutation in the mhRGFP gene. (B). Phase contrast of the same field as in (A).

FIG. 9 is a figure depicting human opal, amber and ochre suppressor serine tRNAs designed according to the invention. (SEQ ID NOS:1–6) As is illustrated, the suppressor tRNAs may be used in tandem using the restriction splice sites indicated.

FIG. 10 is a depiction of human opal suppressor serine tRNA and human amber suppressor serine tRNAs designed according to the present invention and a graphic illustration of the two suppressor tRNAs in tandem using the splice sites indicated. (SEQ ID NOS:5–8)

DETAILED DESCRIPTION OF E INVENTION

Figure 1A:
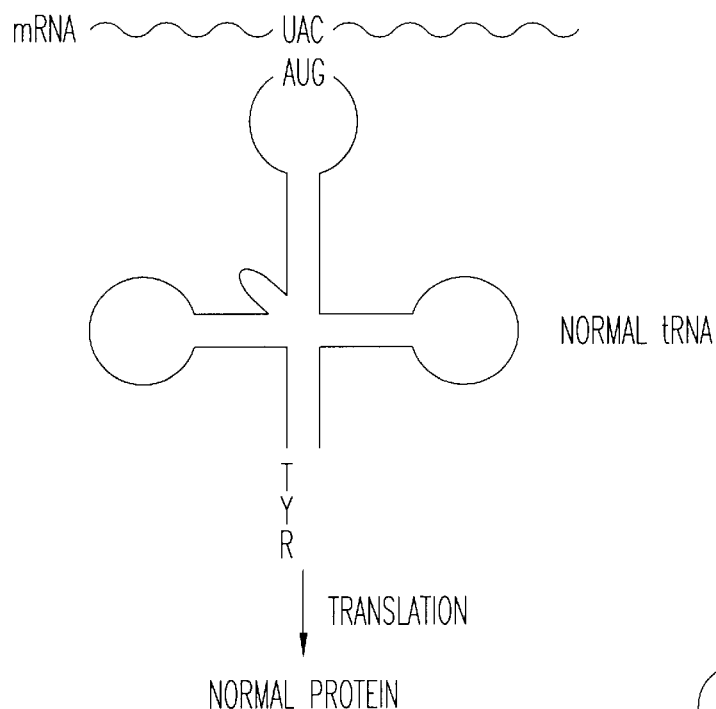
FIGS. 1A, 1B, and 1C are diagrams depicting the basic concepts of the invention.
Figure 1B:
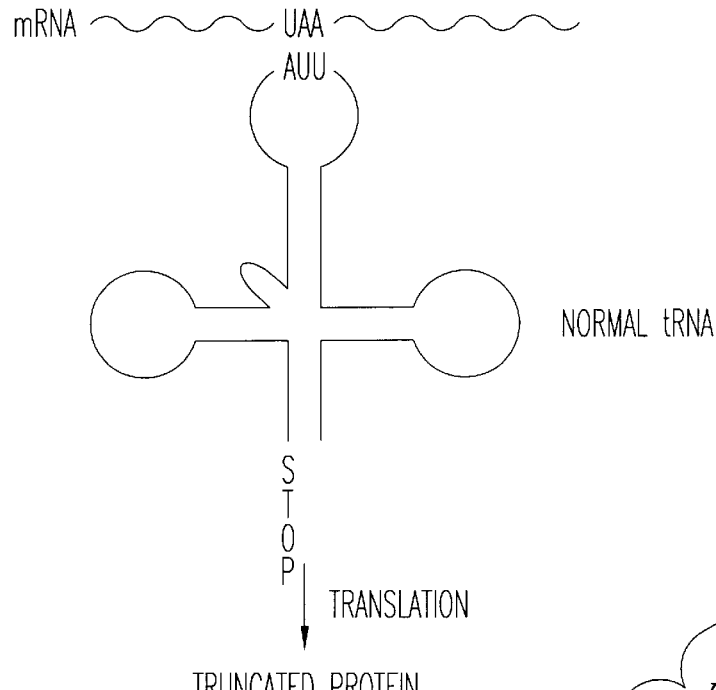
Figure 1C:
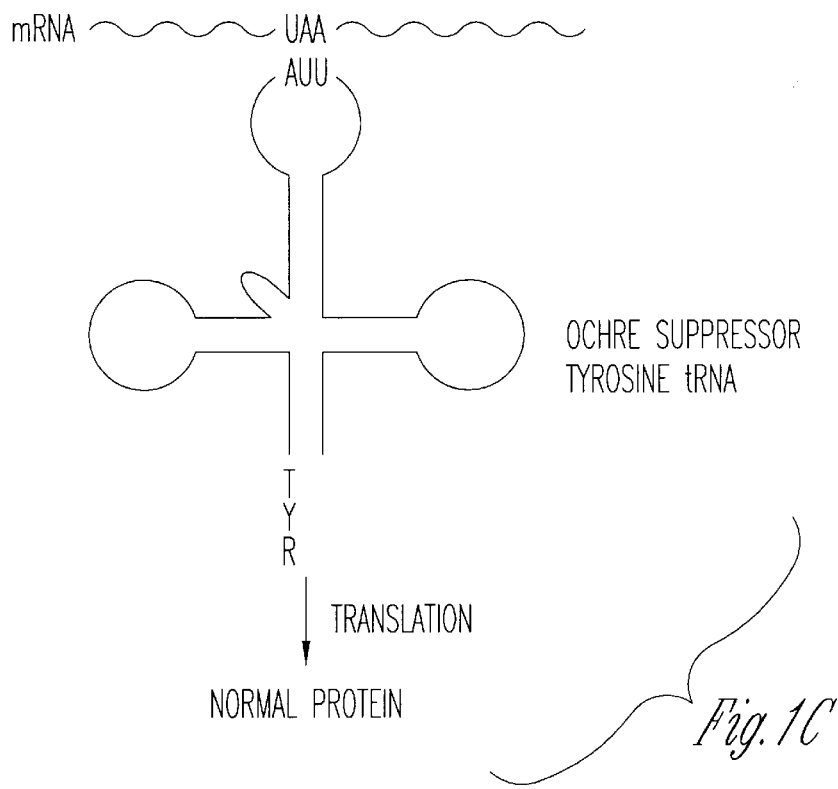

Atkinson and Martin in 1994 identified close to 180 unique point mutations to nonsense codons identified in human genes from a search of literature reports. These types of mutations result in muscular dystrophy, Xeroderma pigmentosum, cystic fibrosis, hemophilia, anemia, hypothyroidism, p53 squamal cell carcinoma, p53 hepatocellular carcinoma, p53 ovarian carcinoma, esophageal carcinoma, osteocarcinoma, ovarian carcinoma, esophageal carcinoma, hepatocellular carcinoma, breast cancer, hepatocellular carcinoma, fibrous histiocytoma, ovarian carcinoma, SRY sex reversal, triosephosphate isomerase-anemia, diabetes and rickets. The BRACA-1 and BRACA-2 genes associated with breat cancer also have similar mutations which may be treated accoding to the teachings herein. The present invention in one embodiment includes methods for treating these diseases by reversing the effects of mutations present that are associated with nonsense mutations through introduction of the synthetic oligonucleotide suppressor tRNAs of the invention.

The nucleotide sequences encoding several human tRNAs are known and generally available to those of skill in the art through sources such as Genbank. See also Sprinzl, Mathias et. Al., Nucleic Acids Research, volume 12, Supplement "compilation of tRNA Sequences" pgs, r1–r57 (1984); Schimmel, P. R., et. Al. Editors, "Transfer-RNA: Structure, Properties, and Recognition, Cold Spring Harbor Labs New York 1979.; Agris, P. F., (1983) "The Modified Nucleosides of Transfer RNA, II, Alan R. Liss Inc., New York (Buckland RA et al., "A cluster of tRNA genes into [DRNI, TRR3, DDRAN] on the short arm of human chromosome 6", *Genomics,* 35 164–171 (1996)). tRNA's have been shown to be highly conserved and are often functional across species thus bacterial or other eucaryotic tRNA sequences are also potential sources for the oligonucleotides of the invention. The determination of whether a particular tRNA sequence will be functional in a desired mammalian cell can be easily ascertained through routine experimentation and the assays and methods discussed or incorporated herein. Further additional potential tRNA sequences as of yet unknown can be ascertained through the assays and protocols discussed as well as the references incorporated herein using routine experimentation.

tRNA genes have strong promoters which are active in all cell types. The promoters for eukaryotic tRNA genes lie within the structural sequences encoding the tRNA molecule itself. Although there are elements which regulate transcriptional activity within the 5' upstream region, the length of an active transcriptional unit may be considerably less than 500 base pairs and thus accommodation within a delivery vector presents no problem. Once they have been transcribed and processed, tRNAs have low rates of degradation. Finally gene therapy with a nonsense suppressor maintains the endogenous physiological controls over the target gene which contains the nonsense codon. One of skill in the art will appreciate that according to the teachings herein, the oligonucleotides of the invention can be used for not just human genetic diseases caused by nonsense mutations but for gene therapy by nonsense suppression to be applicable to mutations in a wide range of genes for site-specific substitution of protein products.

Briefly an oligonucleotide is synthesized which comprises the structural component of a tRNA gene functional in human cells. Thr sequence of this oligonucleotide is designed based upon the known sequence with substitutions made in the anticodon region of the tRNA causing the specific tRNA to recognize a nonsense or other specific mutation. For example as shown in FIG. 2 and according to the invention, the sequence of human serine tRNA having an anticodon of TCG was modified to include a substitution of TCA the complement of the opal mutation to cause the tRNA to recognize the opal stop codon rather than the traditional serine codon.

Importantly the sequences for the oligonucleotides of the invention contain only the structural sequence encoding the tRNA molecule as well as a small portion (around 20 nt) of the 3' flanking region. The 5' region is omitted to result in an oligonucleotide that is small and easier to handle (i.e., around 100 nucleotides long). The oligonucleotide sequence comprises the structural component of the gene and includes around 15 bases from the 3' flanking region and none of the 5' noncoding region. Traditional methods using suppressor tRNAs to date have used entire suppressor tRNA molecules which are isolated, cloned and then site-mutated to create the suppressor tRNA. The present invention provides a much simpler method of designing suppressor tRNAs, namely designing a oligonucleotide sequence comprising the structural sequences encoding the tRNA and a portion of the 3' flanking region only. This small oligonucleotide may then be synthetically synthesized, rather than isolated, using standard genetic engineering techniques and these synthetic suppressor tRNAs can be used according to the methods of the invention. Once designed and shown to be functional according to the assays herein the synthetic suppressor tRNA's can be used in a number of different techniques, the most promising of which is gene therapy.

Suppressor tRNAs are presently being engineered as tools to address basic biological questions. They are being used to site-specifically incorporate unnatural amino acids into proteins in vivo Noren C. J., Anthony-Cahill S. J., Griffith M. C. and Schultz P. G., "A general method for site-specific incorporation of unnatural amino acids into proteins", Science 244:182–188 (1989)) and in combination with electrophysiological techniques, they have provided a general method for structure-function studies of receptors, channels and transporters Nowak M. W., Kearney P. C., Sampson, J. R., Saks, M. E., Labarca G. C. et al., "Nicotinic receptor binding site probed with unnatural amino acid incorporation in intact cells", Science 268:439–442 (1995)). However, suppressor tRNAs are just now being investigated for the treatment of human diseases. Nonsense mutations that occur in key regulatory genes are often deleterious to the cell and responsible for several types of genetic diseases. Atkinson and Martin (Atkinson J. and Martin R., "Mutations to nonsense codons in human genetic disease: implications for gene therapy by nonsense suppressor tRNAs", Nucleic Acids Res. 22:1327–1334 (1994)) surveyed and reported a list of 179 unique point mutations that resulted in nonsense codons that were identified in human genes and caused human genetic diseases. These are all potential targets for gene therapy (in vivo or ex vivo) for treatment of disease with suppressor tRNA technology. The potential application of suppressor tRNA to gene therapy was first demonstrated for β-thalassemia (Temple G. F., Dozy A. M., Roy K. L. and Kan Y. W., "Construction of a functional human suppressor tRNA gene: an approach to gene therapy for β-thalassemia", Nature 296:537–540 (1982)). A human amber suppressor Lysine tRNA was able to suppress the nonsense mutation in mutated β-globin gene, when both were simultaneously expressed in vivo in xenopus oocyte system. The in vivo application of suppressor tRNAs for treatment of genetic diseases caused by nonsense mutation was recently demonstrated in an mdx mouse, which is an animal model for human Duchenne muscular dystrophy with an ochre mutation in dystrophin gene (Li K, Zhang J., Buvoli M., Yan X. D., Leinwand L. and He H., "Ochre suppressor transfer RNA restored dystrophin expression in mdx mice", Life Sciences 61:205–209 (1997)). Direct injection of plasmid DNA encoding the ochre suppressor tRNA into mdx mice produced dystrophin positive fibers. The practical application of suppressor tRNA, as therapeutic agents for gene therapy would largely depend on the development of efficient vectors that can sustain gene expression.

Recently they have served as tools to address basic biological questions such as study of cell-cell interactions during development (Kunes, S. & Steller, H., "Ablation of drosophila photoreceptor cells by conditional expression of a toxin gene", Genes Develop 5, 970–983 (1991)), or to site-specifically incorporate unnatural amino acids into proteins in vivo (Noren, C. J., Anthony-Cahil, S. J., Griffith, M. C. & Schultz, P. G., "A general method for site-specific incorporation of unnatural amino acids into proteins", Science 244, 182–188 (1989)). In combination with electrophysiological techniques, they have provided a general method for structure-function studies of receptors, channels and transporters (Nowak, M. W. et al., "Nicotinic receptor binding site probed with unnatural amino acid incorporation in intact cells", Science 268, 439–442 (1995)).

Additional uses of the invention can include use of the suppressor oligonucleotide tRNAs as triggering molecules to convert inactive toxin molecule into an active toxin molecule. See for example Robinson et al., "Suppression of single and double nonsense mutations induced into the diphtheria toxin A-Chain Gene: a potential binary system for toxin gene therapy", *Human Gene Therapy* 6:137–143 (February. 1995).

Further the oligonucleotides of the invention can be used to institute site-directed mutagenesis of protein products in vitro by introducing missense mutations in gene products to identify structure and function relationships.

According to the invention, human opal, amber, and ochre suppressor serine and arginine tRNAs have been designed which are approximately 100 nucleotides in length and can be introduced to cells to suppress mutations resulting in nonsense codons where a serine or arginine should be present. The oligonucleotides can be introduced directly to recipient cells or can be ligated in tandem to increase efficacy of the oligonucleotide. In yet another embodiment the suppressor tRNA of the invention may be introduced to the cells using standard conventional genetic engineering techniques through use of vectors. Because of the internal promoter sequences of tRNA encoding sequences the tRNA sequence need not be included in a separate transcription unit, although one may be provided.

In a preferred embodiment the nucleotide expression system of the invention is included within an appropriate gene transfer vehicle which is then used to transduce cells to express the suppressor tRNA. The gene delivery vehicle can be any delivery vehicle known in the art and can include simply naked DNA which is facilitated by a receptor mediated transfection as well as any of a number of vectors. Such vectors include but are not limited to eukaryotic vectors, prokaryotic vectors (such as for example bacterial vectors) and viral vectors including but not limited to retroviral vectors, adenoviral vectors, adeno-associated viral vectors, lentivirus vectors (human and other including porcine), Herpes virus vectors, Epstein-Barr virus vectors, SV40 virus vectors, pox virus vectors, pseudotype virus vectors.

In a preferred embodiment, a packaging cell line is transduced with the viral vector containing the nucleic acid sequence to be expressed to form a producer cell line including the viral vector. The producer cells may then be directly administered, whereby the producer cells generate viral particles capable of transducing the recipient cells.

In a preferred embodiment, the viral vector is a retroviral or adenoviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus.

Retroviral vectors are useful as agents to mediate retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

In one embodiment, the retroviral vector may be one of a series of vectors described in Bender, et al., *J. Virol.* 61:1639–1649 (1987), based on the N2 vector (Armentano, et al., *J. Virol.*, 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point.

In Moloney murine leukemia virus (MoMuLV), 5' to the authentic gag start, an open reading frame exists which permits expression of another glycosylated protein (pPr80$^{gag}$). Moloney murine sarcoma virus (MoMuSV) has alterations in this 5' region, including a frameshift and loss of glycosylation sites, which obviate potential expression of the amino terminus of pPr80$^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., *Biotechniques,* 7:980–990, 1989).

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragment or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector includes one or more promoters. Suitable promoters which may be employed include, but are not limited to, the retroviral LTR; the SV40 promoter; and the human cytomegalovirus (CMV) promoter described in Miller, et al., Biotechniques, 7:(9):980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The vector then is employed to transduce a packaging cell line to form a producer cell line. Examples of packaging cells which may be transfected include, but are not limited to the PE501, PA317, Ψ2, Ψ-AM, PA12, T19–14X, VT-19-17-H2, ΨCRE, ΨCRIP, GP+E-86, GP+envAM12, and DAN cell lines. The vector containing the nucleic acid sequence encoding the agent which is capable of providing for the inhibition, prevention, or destruction of the growth of the tumor cells upon expression of the nucleic acid sequence encoding the agent may transduce the packaging cells through any means known in the art. Such means include, but are not limited to, electroporation, the use of liposomes, and $CaPO_4$ precipitation.

The producer cells then are administered directly to or adjacent to desired recipient cells.

In a preferred embodiment the invention comprises a viral vector which commonly infects humans and packaging cell line which is human based. For example vectors derived from viruses which commonly infect humans such as Herpes Virus, Epstein Barr Virus, may be used which do not express an active α-galactosyl envelope.

In a most preferred embodiment the vector comprises a Herpes Simplex Virus plasmid vector. Herpes simplex virus type-1 (HSV-1) has been demonstrated as a potential useful gene delivery vector system for gene therapy, Glorioso, J. C., "Development of Herpes Simplex Virus Vectors for Gene Transfer to the Central Nervous System. Gene Therapeutics: Methods and Applications of Direct Gene Transfer", Jon A. Wolff, Editor, 1994 Birkhauser Boston, 281–302; Kennedy, P. G., "The Use of Herpes Simplex Virus Vectors for Gene Therapy in Neurological Diseases", Q J Med, Noverbem 1993, 86(11):697–702; Latchman, D.S., "Herpes Simplex Virus Vectors for Gene Therapy", Mol Biotechnol, October 1994, 2(2):179–95.

HSV-1 vectors have been used for transfer of genes to muscle. Huard, J., "Herpes Simplex Virus Type 1 Vector Mediated Gene Transfer to Muscle", Gene Therapy, 1995, 2, 385–392; and brain, Kaplitt, M. G., "Preproenkephalin Promoter Yields Region-Specific and Long-Term Expression in Adult Brain After Direct In Vivo Gene Transfer Via a Defective Herpes Simplex Viral Vector", Proc Natl Acad Sci USA, Sep. 13, 1994, 91(19):8979–83, and have been used for murine brain tumor treatment, Boviatsis, E. J., "Long-Term Survival of Rats Harboring Brain Neoplasms Treated With Ganciclovir and a Herpes Simplex Virus Vector That Retains an Intact Thymidine Kinase Gene", Cancer Res, Nov. 15, 1994, 54(22):5745–51; Mineta, T., "Treatment of Malignant Gliomas Using Ganciclovir-Hypersensitive, Ribonucleotide Reductase-Deficient Herpes Simplex Viral Mutant", Cancer Res, Aug. 1, 1994, 54(15):3963–6.

Helper virus dependent mini-viral vectors have been developed for easier operation and their capacity for larger insertion (up to 140 kb), Geller, Al, "An Efficient Deletion Mutant Packaging System for Defective Herpes Simplex Virus Vectors: Potential Applications to Human Gene Therapy and Neuronal Physiology", Proc Natl Acad Sci USA, November 1990, 87(22):8950–4; Frenkel, N., "The Herpes Simplex Virus Amplicon: A Versatile Defective Virus Vector", Gene Therapy. 1. Supplement 1, 1994. Replication incompetent HSV amplicons have been constructed in the art, one example is the pHSVlac vector by Geller et al, Science, 241, September 1988, incorporated herein by reference. These HSV amplicons contain large deletions of the HSV genome to provide space for insertion of exogenous DNA. Typically they comprise the HSV-1 packaging site, the HSV-1 "ori S" replication site and the IE 4/5 promoter sequence. These virions are dependent on a helper virus for propagation.

Primarily two types of mutant helper viruses have been developed to minimize recombination. Other complementary HSV helper virus systems are contemplated herein and are within the scope of those of skill in the art. One such system which has been developed is a temperature-sensitive mutant. An HSV temperature-sensitive (TS) mutant has been developed with a TS mutation in the IE3 gene. Davison et al, 1984, J. Gen. Virol., 65:859–863. Consequently this virus has an IE phenotype, does not replicate DNA, does not significantly alter cellular physiology, and does not produce progeny virus at 37° C. Virus is grown at the permissive temperature of 37° C. TS mutants however have had a tendency to revert to wild type.

In contrast a second helper virus system is a deletion mutant with the majority of the IE3 gene simply deleted. These do not revert to wild type. Therefore HSV-1 vectors packaged using a deletion mutant as helper virus is the most preferred helper virus of the invention. See for example Patterson et al., 1990, J. Gen. Virol., 71:1775–1783. Other replication incompetent helper viruses can be used and one of skill in the art will appreciate that other mutations in the IE genes or other genes which result in a replication incompetent helper virus which will provide the appropriate replication and expression functions and which are coordinated with the helper cell line and vector are contemplated within this invention. Any cell line can be used for this step so long as it is capable of expressing the IE3 or replication dependent gene, or obtaining a helper cell line which has already been transformed and is commercially available. Any cell line can be used by introducing pHE and the plasmid containing the IE3 gene simultaneously. Next, the vector is delivered to the helper cell line by electroporation, calcium phosphate DNA transfection or any other suitable method. Any cell line can be used by introducing pHE and the plasmid containing the IE3 gene simultaneously. The cells are next infected with a helper virus IE3 deletion mutant or other corresponding deletion mutant which is replication incompetent. The IE3 gene or other such gene in the helper cell line complements the helper virus resulting in a productive HSV-1 infection and the resulting virus stock consists of HSV-1 particles containing either vector DNA or helper virus DNA, all of which are replication incompetent. Further information about helper cell lines and the methodology is disclosed in Geller et al., *PNAS*, 87:8950–8954, November 1990, "An Efficient Deletion Mutant Packaging System for Defective Herpes Simplex Virus Vectors: Potential Applications to Human Gene Therapy and Neuronal Physiology". The invention comprises a HSV mini vector which combines a replication incompetent HSV amplicon with other viral sequences such as those from Epstein-Barr virus, human papillomavirus, or bovine papillomavirus type 1 which allow the vector to be maintained in the cell in episomal form achieving a 10 times greater titer, and a very large DNA insert capacity.

One embodiment of the present invention involves a helper virus-dependent mini-viral vector comprising: (a) the HSV-1 "a" sequence for the package/cleavage signal and an "ori S" replication origin for the replication packaging of the plasmid (in response to signals to replicate and package from the helper virus); (b) an Epstein-Barr virus (EBV) nuclear antigen (EBNA-1) gene and an EBV latent origin of replication (ori P) which allow the vector to be maintained in episomal form within the nucleus for replication without integration to the host genome and for even replication into each of two dividing cells; preferably (c) genes from prokaryotic cells for propagation of the vector in *E. coli* (a selectable marker gene such as the ampicillin resistance or tetracycline resistance gene and the col. E1 ori) and (d) a sequence encoding a nonsense suppressor tRNA. Optionally the vector may also comprise prokaryotic genes that provide for a second selectable marker such as the genes for positive Hygromycin selection. As described in U.S. Pat. No. 5,830,727 ioncorporated herein by reference.

In this particular embodiment the packaging function of mini-vector DNA into Herpes simplex viral capsids is provided by a helper virus and a helper cell line.

In yet another embodiment the HSV vector can be engineered to produce a helper free viral vector as in Mann et al., "Construction of a Retro-Virus Packaging Mutant and its Use to Produce Helper-Free Defective Retrovirus", 33 Sal., p. 153–159, May 1983, Journal of Virology, September 1989, pp. 3822–3829, September 1989; Samulski "Helper Free Stocks of Recombinant Adeno-Associated Viruses: Normal Integration Does Not Require Viral Gene Expression"; and Kohn et al., "High Efficiency Gene Transfer Into Mammalian Cells: Generation of Helper-Free Recombinant Retrovirus With Broad Mammalian Host Range", PNAS, 81:6349–6353, October 1984. See also Okasinki, U.S. Pat. No. 4,970,155 "HSV HELPER VIRUS INDEPENDENT VECTOR", incorporated herein by reference.

According to the invention several tRNA synthetic suppressors have been synthesized including a Human ochre suppressor serine tRNA (SEQ ID NO:1), a human amber suppressor serine tRNA (SEQ ID NO:2), a human serine opal suppressor tRNA (SEQ ID NO:3), and a human opal suppressor arginine tRNA (SEQ ID NO:4). These oligonucleotides have been shown to function as active suppressor tRNAs in human cells, providing for read through of nonsense mutations. The invention thus includes these oligonucleotides as well as functional equivalents thereof. Vectors have also been designed which incorporate the oligonucleotides and successfully deliver these to recipient cells according to the invention including pHEhargsuptR-$NA^{Opal}$.

The design of additional oligonucleotides based upon the teachings herein as well as nucleotide delivery vehicles incorporating the same are simply optimization of routine experimental procedures and are intended to be within the scope of this invention.

All references cited herein are hereby expressly incorporated in their entirety by reference. The following examples serve to illustrates the teachings herein and are not intended to limit the invention in any way.

EXAMPLES

Xeroderma pigmentosum (XP), is an autosomal recessive disease with a marked predisposition to sunlight-induced skin cancer and other neurological abnormalities, (Cleaver, J. E., "Defective repair replication of DNA in xeroderma pigmentosum", *Nature* 218, 652–656 (1968)). The disease is characterized by extreme sensitivity to ultraviolet radiation and defective DNA nucleotide excision repair (NER), (Hanawalt, P. C., "DNA repair comes of age", Mutation Res 336, 101–113 (1995); Copeland, N. E., Hanke, C. W. & Michalak, J. A., "The molecular basis of xeroderma pigmentosum", Dermatol Surg 23, 447–455 (1997)). Cell fusion studies to complement DNA repair defects has led to the identification of seven genetic complementation groups of XP, designated XPA—XPG (Cleaver, J. E. & Kraemer, A. L., "Xeroderma Pigmentosum", *The Metabolic Basis of Inherited Disease Vol. II*" (eds Scriver, C. R., L., B. A., Sly, W. S. & Valle, D.) 2949–2971 (McGraw-Hill, New York, 1989)), suggesting that at least seven different gene products are involved in the NER pathway. All of the relevant human genes (XPA, XPB, XPC, XPD, XPE, XPF and XPG) have been identified and mapped to specific chromosomal locations, (Cleaver, J. E. & Kraemer, A. L., "Xeroderma Pigmentosum", *The Metabolic Basis of Inherited Disease Vol. II*" (eds Scriver, C. R., L., B. A., Sly, W. S. & Valle, D.) 2949–2971 (McGraw-Hill, New York, 1989); Tanaka, K. et al., "Analysis of a human DNA excision repair gene involved in group A xeroderma pigmentosum and containing a zinc-finger domain", *Nature* 348 73–78 (1990); Satokata, I., Iwai, K., Matsuda, T., Okada, Y. & Tanaka, K., "Genomic characterization of the human DNA excision repair-controlling gene XPAC", *Gene* 136, 345–348 (1993); Boulikas, T., "Xeroderma pigmentosum and molecular cloning of DNA repair genes", *Anticancer Res* 16, 693–708 (1996)). The cloning and characterization of these DNA repair genes has greatly increased the understanding of NER mechanisms and the relationship between NER molecular defect and the clinical manifestations of XP disease, (Nishigori, C., Moriwaki, S.-i., Takebe, H., Tanaka, T. & Imamura, S., "Gene alterations and clinical characteristics of xeroderma pigmentosum group A patients in Japan", *Arch Dermatol* 130, 191–197 (1994)). This disease was chosen to demonstrate the novel genetic approach to correct the diseased phenotype.

A common approach to correct the XP phenotype defect would be to introduce relevant DNA repair genes into cells derived from XP patients. Several in vitro studies have demonstrated restoration of normal DNA repair phenotype and improved survival after UV irradiation of XP cells following expression of the normal DNA repair gene (Mezzina, M. et al., "Correction by the ERCC2 gene of UV sensitivity and repair deficiency phenotype in a subset of trichothiodystrophy cells", *Carcinogenesis* 15, 1493–1498 (1994); Gozukara, E. M. et al., "The human DNA repair gene, ERCC2 (XPD), corrects ultraviolet hypersensitivity and ultraviolet hypermutability of a shuttle vector replicated in Xeroderma pigmentosum", *Cancer Res* 54, 3837–3844 (1994); Levy, D. D., Saijo, M., Tanaka, K., Kraemer, K. H., "expression of a transfected DNA repair gene (XPA) in xeroderma pigmentosum group A cells restores normal DNA repair and mutagenesis of UV-treated plasmids", *Carcinogenesis* 16, 1557–1563 (1995); Yagi, T. et al., "Complete restoration of normal DNA repair characteristics in group F xeroderma pigmentosum cells by over-expression of transfected XPF cDNA", *Carcionogenesis* 19, 55–60 (1998)). Other investigators have complemented the defect by introducing DNA repair genes from other organisms such as mouse, yeast, and Drosophila, (Tanaka, K., Satokata, I., Ogita, Z., Uchida, T. & Okada, Y., "Molecular cloning of a mouse DNA repair gene that complements the defect of group-A xeroderma pigmentosum", *Proc Natl Acad Sci, USA,* 86, 5512–5516 (1989); Lambert, C., et al., "A yeast DNA repair gene partially complements defective excision repair in mammalian cells", *EMBO J* 7, 3245–3253 (1988); Shimamoto, T., et al., "Expression and functional analyses of the Dxpa gene the drosophila homolog of the human excision repair gene XPA", *J Biol Chem* 270, 22452–22459 (1995)). Another useful approach would be to correct the genetic defect in the DNA repair gene or its transcript and thereby restore a normal phenotype. Molecular genetic studies have defined novel deletions, splicing, point mutations and nonsense mutations in the XP group A complementing (XPAC) gene, (Satokata, I. et al., "Characterization of a splicing mutation in group A xeroderma pigmentosum", *Proc Natl Acad Sci, USA* 87, 9908–9912 (1990); Satokata, I., et al., "Three nonsense mutations responsible for group A xeroderma pigmentosum", *Mutation Res* 273, 193–202 (1992); Satokata, I., Tanaka, K. & Okada, Y., "Molecular basis of group A xeroderma pigmentosum: a missense mutation and two deletions located in a zinc finger consensus sequence of the XPAC gene", *Hum Genet* 88, 603–607 (1992); Satokata, I., Tanaka, K., Yuba, S. & Okada, Y., "Identification of splicing mutations of the last nucleotides of exons a nonsense mutation and a missense mutation of the XPAC gene as causes of group A xeroderma pigmentosum", *Mutation Res* 273, 203–212 (1992)). The genetic defect caused by nonsense mutations could be repaired by expressing suppressor tRNAs that recognize the premature termination signal, thereby resulting in the insertion of its corresponding amino acid and restoration of normal phenotype in accordance with the teachings of the present invention.

Materials and Methods

Cells lines. DNA repair proficient human fibroblast cell line (VA13, an SV40 transformed human W138 fibroblast cell line, ATCC, Gaithersburg, Md.) and an SV40 transformed cell line established from a XP patient (XP12ROSV; a kind gift from Dr. Tanaka, Japan), were used for study. The cells were grown in Dulbecco's modified Eagle's medium (DMEM; Gibco BRL, Gaithersburg, Md.) supplemented with 1% glutamine and 10% fetal bovine serum (DIV medium). Cells were grown at 37° C. in a humidified $CO_2$ incubator. E5 helper cells are green monkey kidney cells that express the IE3 gene and allow the replication of the IE3-deleted helper virus (kindly provided by P. Johnson, San Diego).

Transfection. Using FuGENE 6 reagent (Boehringer Manheim, Germany) transfection was carried out as per manufacturer instructions with minor modifications. Cells ($\sim$1.5–2$\times$10$^5$) were seeded in 60 mm tissue culture plates and allowed to attach for 16–20 h. FuGENE 6 transfection reagent (12 μl) was incubated for 5 minutes at room temperature (RT) in 88 μl opti-MEM medium (Gibco BRL.), then added to the plasmid DNA (4 μg) and further incubated for 15 minutes at RT. This transfection mixture was added to the cells grown in complete DMEM medium (2 ml). After 14–16 hours at 37° C., the cells were washed once with Hanks balanced salt solution (HBSS) and then fed with complete medium and further incubated at 37° C. for a total of 72 hours after transfection. Transfected cells were selected in the presence of hygromycin (100–150 μg/ml).

Figure 2A:
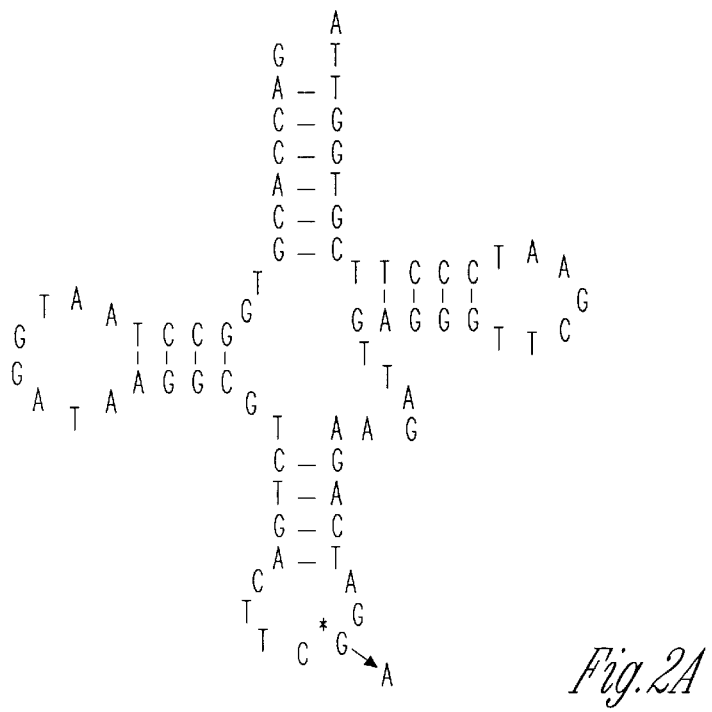
FIGS. 2A and 2B are diagrams depicting Suppressor tRNA and expression vector constructs.
Figure 2B:
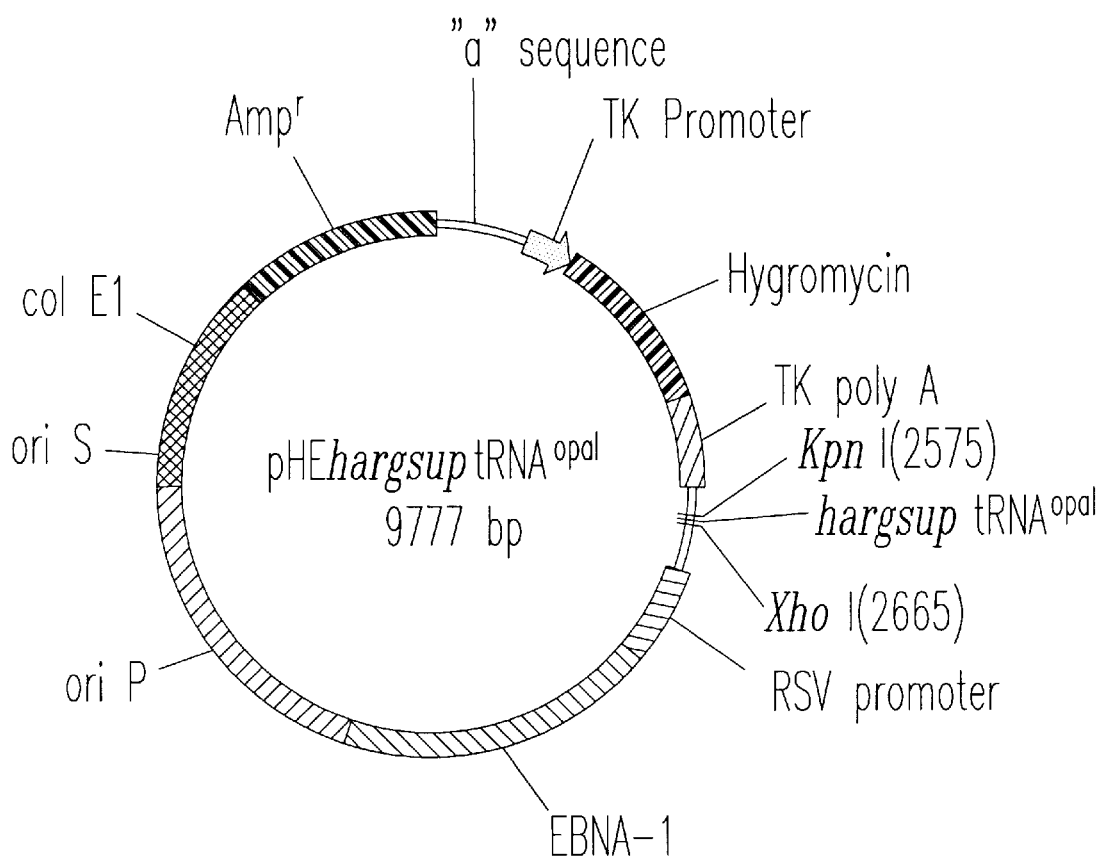

Construction of human arginine opal suppressor tRNA (hargsup tRNA$^{Opal}$) and subcloning into a herpes simplex virus (HSV amplicon vector. Based on the reported nucleotide sequence of human arginine tRNA gene (Buckland RA et al., "A cluster of tRNA genes into [DRNI, TRR3, DDRAN] on the short arm of human chromosome 6", *Genomics*, 35 164–171 (1996)), the arginine opal suppressor tRNA was constructed that contained the structural sequences encoding the tRNA molecule and 15 bases from the 3' flanking region. The 3' flanking region contains clusters of T residues in the noncoding strand that act as the signal to terminate transcription. The sequence (noncoding strand) and the clover leaf structure of the human arginine tRNA is as shown in FIG. 2A. A single base change (shown with * in FIG. 2A) in the anticodon was introduced to convert the human arginine tRNA into an opal suppressor tRNA. A pair of overlapping oligonucleotides: 5'-GCGCTCGAGAAAACGAAC CCCACTTAACCA-CGAAGGGATTCGAACCCTCAATCTTCTGATC-3' (SEQ ID NO:15) and 5'-GCGGGT ACCGACC-ACGTGGCCTAATGGATAAGGCGTCTGACTTCAGAT-CAGAAGATTGAGGG-3' (SEQ ID NO:16) (synthesized by Integrated DNA Technologies, Inc., Coralville, Iowa) were annealed and filled in using T7 DNA polymerase (Sequenase Version 2, United States Biologicals) enzyme and a reaction mixture containing all four deoxynucleotides. The double stranded oligonucleotide was digested with Kpn I/Xho I and ligated at the same restriction sites into an HSV amplicon (Wang, S., Young, W.-B., Jacobson, C. & Link, C. J., "A novel Herpesvirus amplicon system for in vivo gene therapy", *Gene Ther* 4, 1132–1141 (1997)) vector that was modified to remove the CMV promoter and the poly A sequences. The resulting expression vector pHEhargsup tRNA$^{Opal}$ is as shown in FIG. 2B. The expression vector contains an EBV ori P and EBNA sequence to maintain the plasmid episomally and a hygromycin resistance gene to permit selection of transfected mammalian cells. The plasmid also contains the HSV-1 lytic replication origin (ori S) and a HSV-1 terminal packaging signal "A" sequences for replication and packaging into HSV-virions in the presence of transacting helper virus (Wang, S., Young, W.-B., Jacobson, C. & Link, C. J., "A novel Herpesvirus amplicon system for in vivo gene therapy", *Gene Ther* 4, 1132–1141 (1997); Spaete, R. R. & Frenkel, H., "The herpes simplex virus amplicon: A new eucaryotic defective-virus cloning-amplifying vector", *Cell* 30, 295–304 (1982); Wang, S. & Vos, J., "A hybrid infectious vector based on Epstein-Barr virus and Herpes simplex virus type I for gene transfer into Human Gene", *J Virol* 70, 8422–8430 (1996)).

Introducing an opal (TGA) mutation at a defined position within a humanized red-shifted green fluorescent protein (hRGFP) gene. An opal mutation was introduced at position Arg(CGC)730pal(TGA) in the hRGFP gene (Levy, J. P., Muldoon, R. R., Zolotukin, S. & Link, C. J., "Retroviral transfer and expression of humanized, red shifted green fluorescent protein into human tumor cells", *Nature Biotechnol* 14, 610–614 (1996)). The mutation was introduced by PCR and sequenced to confirm the mutation. The opal-mutated hRGFP was subcloned into the pHE700 HSV amplicon vector (Wang, S., Young, W.-B., Jacobson, C. & Link, C. J., "A novel Herpesvirus amplicon system for in vivo gene therapy", Gene Ther 4, 1132–1141 (1997)), under the control of the CMV promoter (mnRGFP).

Northern Analysis. Total RNA was isolated from cultured cells using the RNeasy Total RNA kit (Qiagen, Santa Clarita, Calif.). RNA samples (10 g) were separated by electrophoresis through 1% formaldehyde agarose gels and transferred onto nytran membrane filters (Schleicher & Schuell, Keene, N.H.). The filters were pre-hybridized for 2 hours at 42° C. in hybrisol I solution (Oncor, Gaithersburg, Md.) and then hybridized overnight at 42° C. with probes labeled with a (Atkinson, J. & Martin, R., "Mutations to nonsense codons in human genetic disease: implications for gene therapy by nonsense suppressor tRNAs", *Nucleic Acids Res* 22, 1327–1334 (1994)) PdCTP using the Random Primed DNA labeling kit (Boehringer Mannheim). The filters were washed twice with 2×SSC, 0.1% SDS at RT, then 0.1×SSC and 0.1% SDS at 55° C. for 30 minutes and autoradiographed.

Western Analysis. Cultured cells were washed twice with phosphate-buffered saline (PBS) and then lysed in 50 mM Tris-HCI, pH 7.5, 0.15 M NaCl, 1% Nonidet P-40, 0.1% SDS and containing protease inhibitors phenylmethylsulfonylfluoride (100 $\mu$g/ml), aprotinin (1 $\mu$g/ml) and leupeptin (1 $\mu$g/ml). The cell lysate was incubated on ice for 20 minutes, centrifuged at 10,000×g for 10 minutes at 4° C. and the supernatant collected. Samples (30 $\mu$g) were mixed with 6 $\mu$l or 5×sample buffer (Laemmli, 1970), boiled for 3 minutes and separated by SDS-PAGE. Protein samples were electroblotted onto nitrocellulose membrane and probed with specific antibodies. The GFP and XPAC proteins were detected by Enhanced Chemiluminescence (Amersham, England), using anti-GFP (Clontech, Palo Alto, Calif.) and anti XPAC (Santa Cruz Biotechnology, Inc., Santa Cruz, Calif.) polyclonal antibodies respectively and horseradish peroxidase (HRP)-conjugated anti-rabbit immunoglobulin as second antibody.

Clonogenic assay. For UV survival experiments, three cell lines- VA13, XP12ROSV and XP12ROSV expressing the hargsup tRNA$^{Opal}$ were plated in triplicates in 60 mm plates at different cell densities ranging from 2.5×10$^2$ to 1×10$^6$ in 60 mm petri plates, depending on the cell line and UVC dose used. The next day the cells were rinsed with PBS and exposed to UVC dose (254 nm, Spectroline, model XX-15G, Spectronics Corp, NY) ranging from 0–6 J/m$^2$. The PBS buffer was removed and replaced with complete DMEM medium containing vitamins and nonessential amino acids. Approximately 10–12 days after irradiation the colonies were fixed with formaldehyde and stained with crystal violet (0.05% in water). The percent colony-forming ability was determined by comparing the colony counts of the irradiated plates with those of the unirradiated plates. Separate experiments were independently repeated two to three times.

Reactivation assay using plasmid carrying chloramphenicol acetyl transferase (CAT) reporter gene. Plasmid pSVCAT (control vector; Promega, Madison, Wis.) expressing the CAT gene under the control of SV promoter was used for plasmid reactivation studies. CAT assays were performed using the manufacturer's protocol with minor modifications. Plasmid DNA (20 $\mu$g/ml) in water was treated with 254 nm UVC radiation at dose ranging from 0–600 J/m$^2$, ethanol precipitated and resuspended in suitable volume for transfection. XP12ROSV cells (2×10$^5$) were seeded in 60 mm plate and on the next day were cotransfected with pHEhargsup tRNA$^{Opal}$ and UVC irradiated pSVCAT plasmid DNA in a 10:1 ratio (4 $\mu$g of total DNA). As control for CAT plasmid reactivation, DNA repair proficient VA13 cells (positive control) and XP12ROSV cells (negative control) seeded in 60 mm plate were cotransfected with the modified pHE vector and the UVC irradiated pSVCAT plasmid in the ratio of 10:1. After 72 hours, the cells were harvested and lysed by three freeze-thaw cycles. Lysates were analyzed for CAT activity using a liquid scintillation counting (LSC) method. Briefly, reaction mixture containing protein lysates, [15C] chloramphenicol (Du Pont New England Nuclear, Wilmington, Del.; NEC 408A, 0.15 $\mu$Ci) and n-butyryl CoA (25 $\mu$g as substrate (final reaction volume of 125 $\mu$l) was incubated at 37° C. for 3 hours. The reaction products were extracted with 300 $\mu$l of mixed xylene. The upper xylene phase was collected and extracted twice more by adding 100 $\mu$l of 0.25 M Tris-HCI, pH 8.0. A fixed amount of the upper xylene phase that represents the butyrylated chloramphenicol product was added to the scintillation fluid (5 ml; OptiScint "HiSafe"l LKB, England) and counted by liquid scintillation spectrometry. Individual transfections were carried out in duplicate and separate experiments were independently repeated two to three times. The ability to reactivate the UVC irradiated plasmid was defined as the ratio of the CAT activity in extracts from cells transfected with the UV irradiated plasmid to that in cells transfected with the non-irradiated pSVCAT plasmid.

Packaging of pHEhargsup tRNA$^{Opal}$ amplicon vector. E5 cells (2×10$^6$ cells/10 cm dish) were transfected with the pHEhargsup tRNA$^{Opal}$ vector. Two days following transfection the cells were placed under selection with hygromycin B (150 $\mu$g/ml). The hygromycin-resistant E5 cells were super-infected with 1 MOI of CgalΔ3 helper virus (kindly provided by P. Johnson, San Diego) in 1 ml of Opti-MEM medium. The viruses were allowed to adsorb on the cells for 2 hours at 37° C. in a humidified, 5k $CO_2$ incubator and then 9 ml of DEM medium with 10% FBS was added and the cells further incubated for 50–60 hours. The viral supernatant containing cell debris was collected. The cells were lysed by freeze-thaw method (repeated three times), then centrifuged at 2400×g to pellet the cell debris. The titer of CgalΔ3 helper virus was determined by 5-bromo-4-chloro-3-indolyl-β-D-galactopyranoside (X-gal) staining, as described previously (Wang, S., Young, W.-B., Jacobson, C. & Link, C. J., "A novel Herpesvirus amplicon system for in vivo gene therapy", *Gene Ther* 4, 1132–1141 (1997)). To demonstrate in vitro transfer of the pHEhargsup tRNA$^{Opal}$ amplicon vector, XP12ROSV cells expressing the mhRGFP gene were transduced with different amounts of the viral supernatant diluted in opti-MEM and incubated at 37° C. in a humidified 5% $Co_2$ incubator. After 24 hours the cells were visualized for restoration of GFP fluorescence.

Results

Restoration of GFP fluorescence by suppressor tRNA. To test the functional activity of the hargsup tRNA$^{Opal}$, mhRGFP was used as a reporter gene. An opal mutation introduced at position Arg73 Opal in hRGFP gene completely prevents detectable GFP fluorescence. However, cotransfection of the plasmid containing the hargsup tRNA$^{O}_{pal}$ with the plasmid containing the mhRGFP gene in XP12ROSV cells, was able to suppress the opal mutation in mhRGFP and restore GFP fluorescence (FIG. 3A and 3B). Control transfections with mhRGFP plasmid alone did not exhibit any GFP fluorescence (FIG. 3C and 3D).

Expression of GFP transcripts and protein. To determine the expression of the hRGFP and mhRGFP transcripts in transfected XP12ROSV cells, northern blots were probed with the hRGFP cDNA. Transcripts of similar size were observed in both the transfected cell lines (FIG. 4A, top panel). After normalization with the CAPDH housekeeping gene (FIG. 4A, bottom panel), mhRGFP transcripts were approximately one third less abundant compared to the hRGFP transcripts. Western analysis using anti-GFP antibody showed that XP12ROSV cells cotransfected with mhRGFP and hargsup tRNA$^{Opal}$ expressed a full-length GFP protein similar in size to the hRGFP protein (FIG. 4B). Thus providing direct evidence that hargsup tRNA$^{Opal}$ can suppress the nonsense mutation in the mhRGFP gene and produce a full-length functional protein. Although equal amounts of the protein were loaded (data not shown), an approximate 10-fold reduction in signal intensity was observed in the XP12ROSV cells transfected with both the mhRGFP and hargsup tRNA$^{Opal}$ compared to hRGFP alone. Two observations account for the much lower detected hRGFP protein found in the cells co-transfected with both the mhRGFP and hargsup tRNA$^{Opal}$. The level of mhRGFP transcript targets for the suppressor tRNA were about one third less in abundance relative to expression of a housekeeping gene (FIG. 4A). However, the reduction in protein level was significantly greater than the decrease in RNA transcripts indicating an additional effect from relatively low suppression efficiency. XP12ROSV cells transfected with the mhRGFP gene alone should produce a truncated (~8 kDa) GFP protein but this was not detected because of the gel system used.

Figure 5:
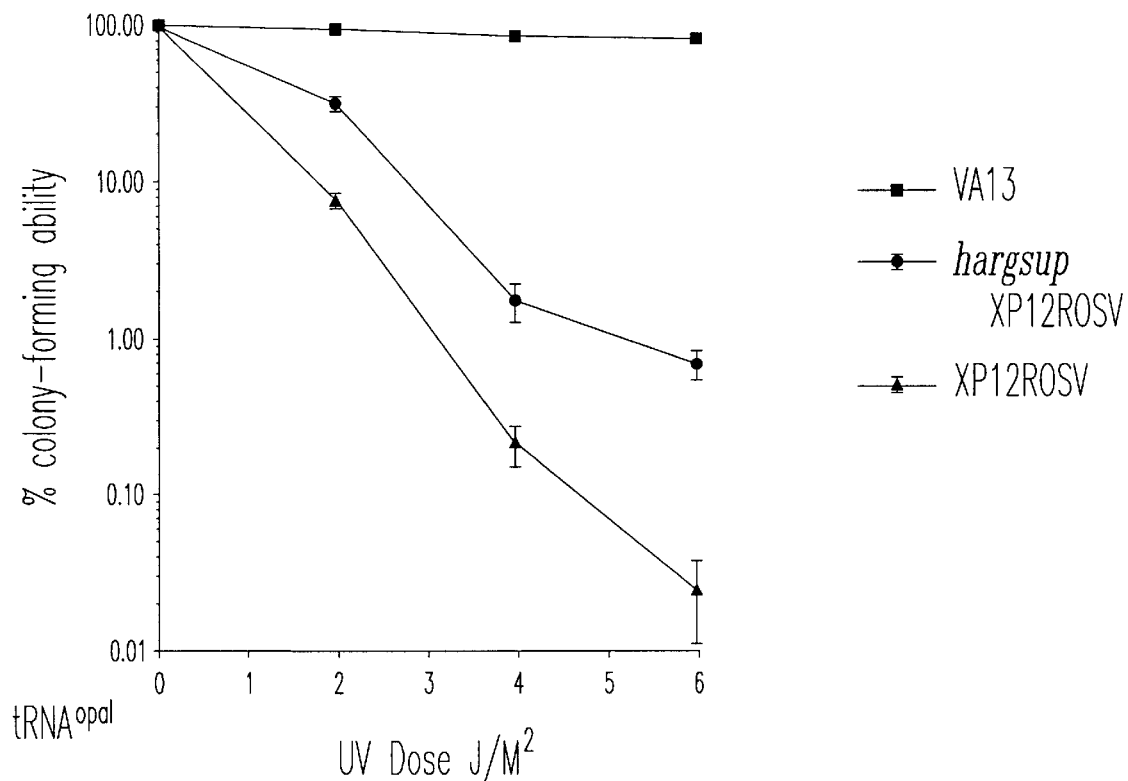
FIG. 5 is a graph depicting the partial correction of the DNA repair deficient phenotype by suppressor tRNA. VA13, XP12ROSV and XP12ROSV cells expressing the hargsup tRNA$^{Opal}$ were seeded at varying cell densities from $2.5 \times 10^2$ to $1 \times 10^6$, depending upon the cell line and UVC irradiation dose used. The following day, cells were rinsed with PBS and irradiated with UVC (254 nm) light at 0 to 6 J/m$^2$. Approximately 10 to 12 days after irradiation the cells were fixed and stained with crystal violet. The percent colony-forming ability was determined by comparing the colony counts of the irradiated plates with those of the unirradiated plates and plotted against UVC dose used. A 4 to 35 fold increase in the colony forming ability at higher UV doses was observed in XP12ROSV cells expressing the hargsup tRNA$^{Opal}$.

Correction of XPA NER deficiency phenotype in XP cell lines by nonsense suppressor tRNA as measured by post UV irradiation cell survival. To demonstrate in vitro that suppressor tRNAs can repair genetic defects caused by nonsense mutations, a DNA repair-deficient XP fibroblast cell line -XP12ROSV was selected. A C to T transition at nucleotide 619 in exon 5 of the XPAC gene altered Arg-207 codon (CGA) to a nonsense codon (TGA). Thus resulting in the truncated XPAC protein and disruption of the functional activity of the XPAC gene (Satokata, I., et al., "Three nonsense mutations responsible for group A xeroderma pigmentosum", Mutation Res 273, 193–202 (1992)). This cell line has a low colony forming ability after UV irradiation. These cells were transfected with the pHEhargsup tRNA$^{Opal}$ plasmid and selected with hygromycin. The selected cells were irradiated with UVC (254 nm) at doses ranging from 0–6 J/m$^2$. Clonogenic assay was performed and a 4 to 35 fold increase in the colony-forming ability at higher UV doses was observed in XP12ROSV cells expressing the hargsup tRNA$^{Opal}$ (FIG. 5). The results demonstrated an improved UV survival of the XP12ROSV cells due to partial correction in the DNA repair deficiency phenotype by the introduction of the suppressor tRNA.

Figure 6:
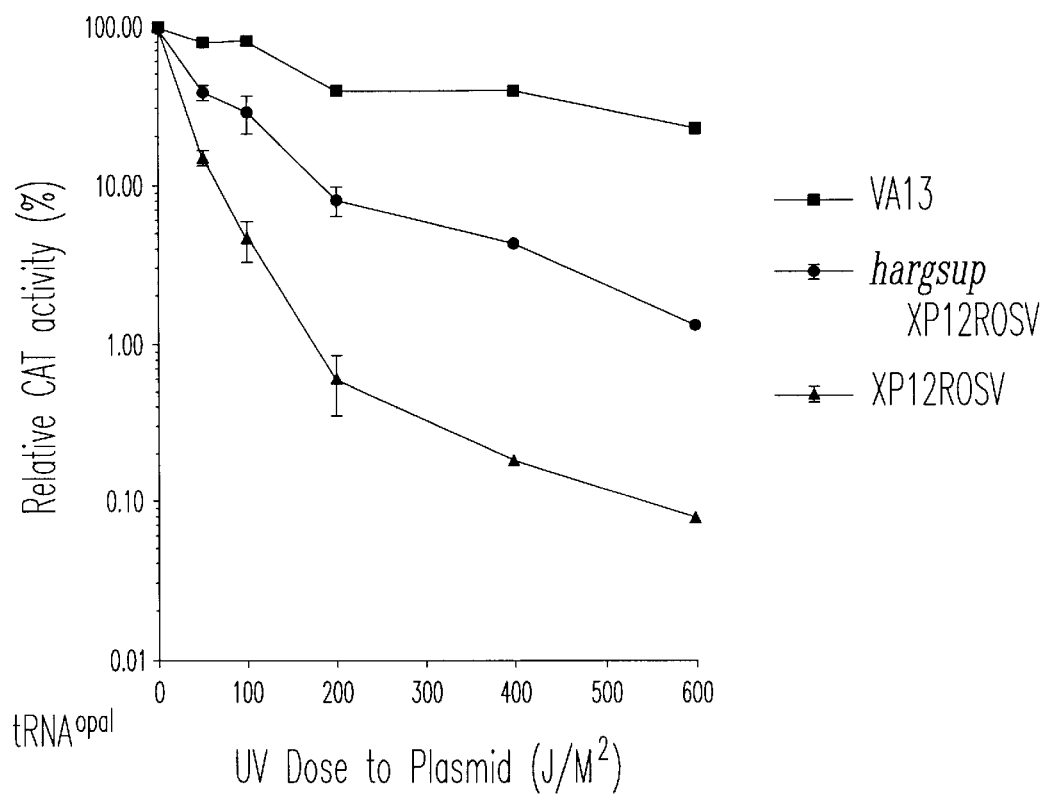
FIG. 6 is a graph which depicts the correction of defective repair of pSVCAT plasmid. XP12ROSV cells were transiently cotransfected with the UVC irradiated pSVCAT and pHEhargsup tRNA$^{Opal}$ plasmids. As controls VA13 cells (positive control) and XP12ROSV cells (negative control) were cotransfected with UVC irradiated pSVCAT plasmid and pHE vector alone. After 72 hours, cell lysates were obtained and analyzed for CAT activity using the liquid scintillation counting (LSC) method. CAT activity in cell extracts was expressed as percent of the activity in cells transfected with unirradiated PSVCAT and plotted against UVC irradiation dose used to inactivate the pSVCAT plasmid. XP12ROSV cells expressing the hargsup tRNA$^{Opal}$ showed a 3 to 17 fold increased ability to reactivate UV irradiated pSVCAT plasmid compared to XP12ROSV cells transfected the irradiated pSVCAT plasmid alone.
Figure 11:
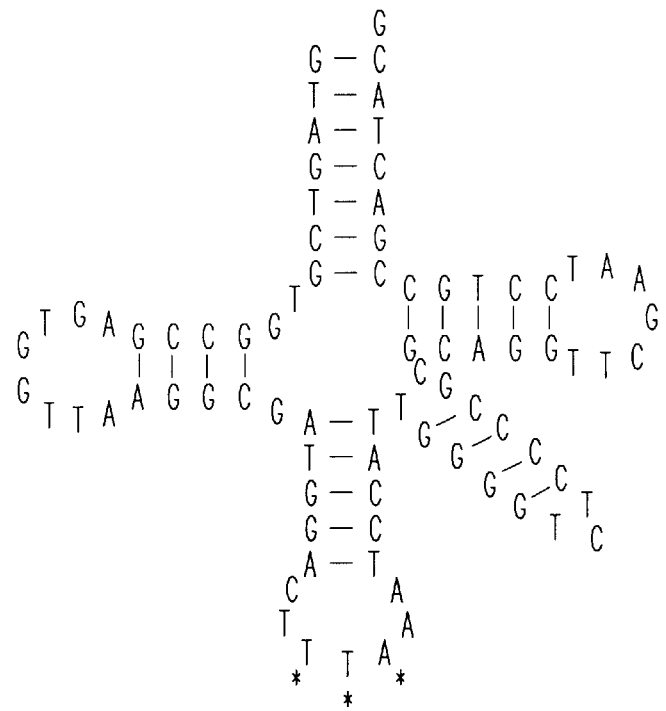
FIG. 11 is a diagram depicting the cloverleaf structure formed by the novel human ochre suppressor serine tRNA of the invention. (SEQ ID NO:9)
Figure 12:
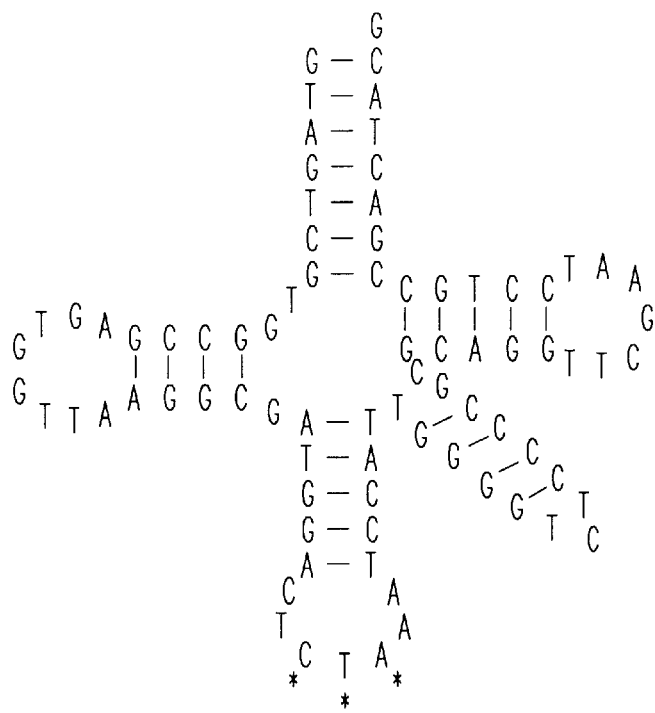
FIG. 12 is a diagram depicting the cloverleaf formation in the anticodon region of yet another synthetic amber suppressor serine tRNA formed in accordance with the present invention. (SEQ ID NO:10)
Figure 13:
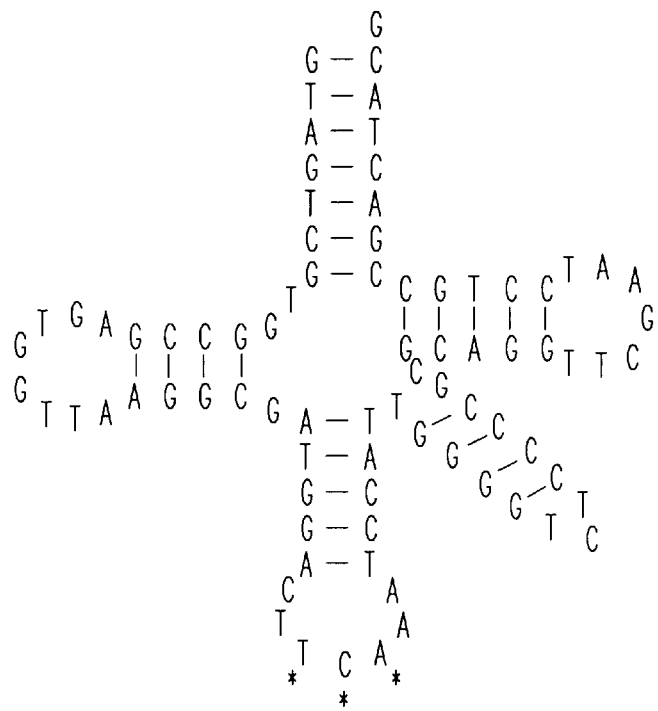
FIG. 13 is a drawing depicting the cloverleaf formation of yet another human serine opal suppressor tRNA illustrating the anticodon region in accordance with the present invention. (SEQ ID NO:11)
Figure 14:
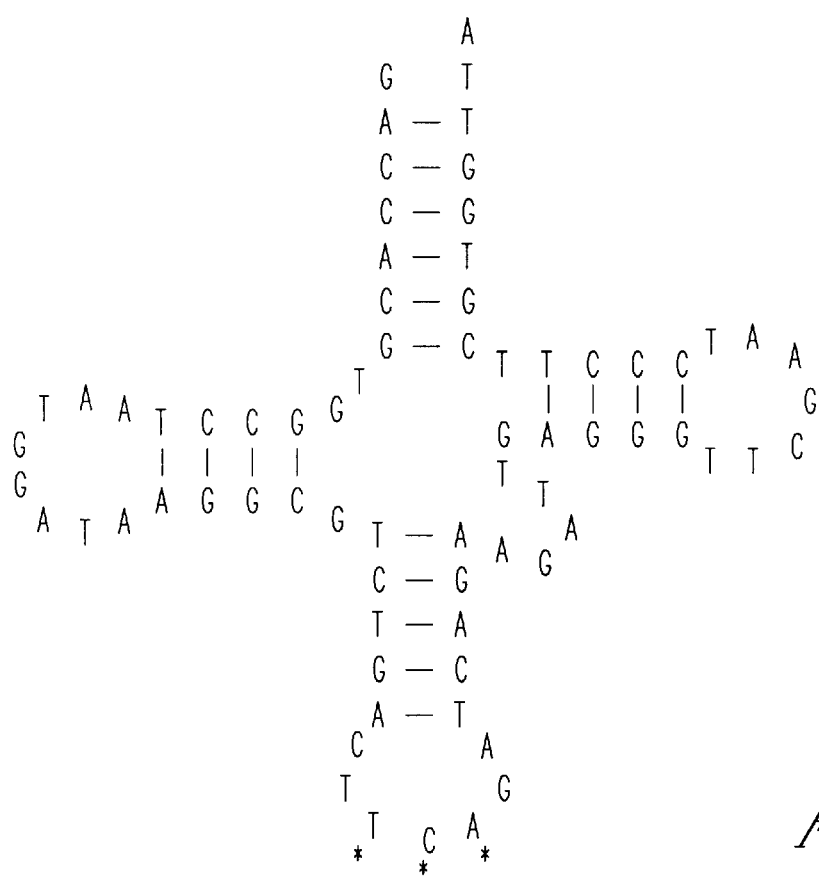
FIG. 14 is a drawing depicting the cloverleaf and anticodon regions formed by yet another human opal suppressor tRNA by the present invention. (SEQ ID NO:12)

UV irradiated CAT plasmid reactivation studies. An alternative in vitro test to determine if suppressor tRNAs can suppress the XPAC gene nonsense mutation in XP12ROSV cells and restore DNA repair activity is the use of expression vectors. Plasmid vectors expressing the bacterial CAT gene has been widely used to measure DNA repair and mutagenesis in human cells (Kraemer, K. H., Protic-Sabljic, M., Bredberg, A. & Seidman, M. M., "Plasmid vectors for study of DNA repair and mutagenesis", Curr Probl Derm 17, 166–181 (1987)). The XP12ROSV cells transiently transfected with the UV irradiated pSVCAT plasmid were much more sensitive to inhibition of CAT expression compared to the normal VA13 cells (FIG. 6). However, transient expression of suppressor tRNA in XP12ROSV cells results in an increased ability to reactivate UV irradiated pSVCAT plasmid by efficiently suppressing the nonsense mutation in XPAC gene and restoring the DNA repair activity. A 3 to 17 fold increase in the CAT activity at higher UV doses was observed in XP cells transiently transfected with both the pHEhargsup tRNA$^{Opal}$ plasmid and UV damaged pCAT plasmid (FIG. 6).

Levels of XPAC transcript and XPAC protein in XP cells. Northern analysis of XP12ROSV cells showed a very low abundance of the XPAC transcript compared to the normal DNA repair proficient VA13 cells (FIG. 7A, top panel). The results obtained were similar to those reported earlier (Satokata, I., et al., "Three nonsense mutations responsible for group A xeroderma pigmentosum", Mutation Res 273, 193–202 (1992)). To correlate the partial phenotypic correction in XP12ROSV cells by suppressor tRNA with the presence of full-length protein, Western analysis was performed. FIG. 7B shows that XPAC protein while detectable in the normal VA13 cells, was not detectable in XP12ROSV cells transfected with the hargsup tRNA$^{Opal}$. Furthermore, no truncated XPAC polypeptide was observed in the XP12ROSV cells.

Transduction of XP12ROSV cells expressing mhRGFP with pHEhargsup tRNA$^{Opal}$ amplicon vector packaged into HSV-1 virions. The pHEhargsup tRNA$^{Opal}$ amplicon vector packaged into HSV-1 virions could successfully transduce and suppress nonsense mutation in the mhRGFP gene expressed in XP12ROSV cells, as visualized by restoration of GFP fluorescence (FIG. 8A and 8B). At 40 MOI of helper virus, restoration of GFP fluorescence was observed in approximately 5% of cells. However substantial cytotoxicity was evident by 24 to 48 hours after infection. At lower MOI of infection no GFP positive cells were observed. GFP fluorescence was not detected with the above cell line was transduced with the pHE700 TK vector packaged into HSV-1 virions, used as negative control or when XP12ROSV cells were transduced with the pHEhargsup tRNA$^{Opal}$ amplicon vector alone (data not shown).

Discussion.

Using Xeroderma Pigmentosum group A cells as a disease model, we have been able to demonstrate in vitro partial restoration of the DNA repair activity of the nonsense mutated XPAC gene. The XP12ROSV cell line used for study contains a homozygous nonsense mutation in the XPAC gene (Satokata, I., et al., "Three nonsense mutations responsible for group A xeroderma pigmentosum", Mutation Res 273, 193–202 (1992)). An arginine (CGA) codon had been mutated to an opal (TGA) codon in the XPAC gene, hence for our study we chose to construct a human arginine opal suppressor tRNA. To date, no tRNA suppressors had previously been derived from the human arginine tRNA. The designed suppressor tRNA is small in size as the 5' flanking sequences have been deleted while 15 bases from 3' flanking sequences were retained to signal transcription termination. The construction of small-sized tRNAs by using a pair of oligonucleotides has an advantage over the more tedious and time consuming method of site-directed mutagenesis to convert tRNA into a suppressor tRNA. Using our method we have constructed several different functional suppressor tRNAs such as human serine amber suppressor and tyrosine ochre suppressor tRNA. A high readthrough efficiency using amber or ochre mutated hRGFP as a reporter gene was also observed by FACS analysis of GFP fluorescence (data not shown).

The functional activity of the hargsup tRNA$^{Opal}$ was first established using an opal mutated humanized red-shifted green fluorescent protein as a reporter gene. A high efficiency of nonsense suppression (>80%) was demonstrated by the restoration of hRGFP fluorescence and by FACS analysis for GFP positive cells (data not shown). Expression of the hargsup tRNA$^{Opal}$ in XP cell lines produced a 4 to 35 fold increase in cell survival after UV irradiation and increased ability of XP cells to reactivate UV-irradiated pSVCAT plasmid.

Suppressor tRNAs may cause readthrough of the natural termination codons. The C terminal extended proteins may have codominant negative properties, or they may have severely limited activity or they may be subjected to premature degradation. All of which may be deleterious to the cell. However, the cell may be able to safeguard itself from such harmful effects because of multiple translational stop codons at the end of the gene and also due to the inefficient suppression by the different suppressor tRNAs. Preliminary studies from our toxicity assay revealed that stable expression of suppressor tRNA in XP cells did not alter the cycle as determined by FACS analysis (data not shown) or cause a direct cytotoxic affect that could be detected in clonogenic assays.

The practical application of suppressor tRNA, as therapeutic agents for gene therapy will be highly dependent on the development of efficient vectors that can sustain long term gene expression in the appropriate target tissues or cells. Several types of vectors are under development for this purpose. Use of recombinant retroviruses to deliver DNA repair genes such as XPD (Carreau, M., et al., "Functional retroviral vector for gene therapy of xeroderma pigmentosum group D patients", *Hum Gene Ther* 6, 1307–1315 (1995); Quilliet, X., et al., "Long-term complementation of DNA repair deficient human primary fibroblasts by retroviral transduction of the XPD gene", *Mutation Res* 364, 161–169 (1996)), XPA, XPB and XPC genes (Zeng, L. et al., "Retrovirus-mediated gene transfer corrects DNA repair defect of xeroderma pigmentosum cells of complementation groups A, B and C", *Gene Ther* 4, 1077–1084 (1997) in the XP cells with the corresponding defective DNA repair gene has been reported. Functional expression of the transgene and correction of DNA repair activity was observed in the transduced cells. To obtain efficient delivery of the suppressor tRNA we chose to use a novel HSV amplicon vector, pHE, (Wang, S., Young, W.-B., Jacobson, C. & Link, C. J., "A novel Herpesvirus amplicon system for in vivo gene therapy", *Gene Ther* 4, 1132–1141 (1997) so that the plasmid containing the suppressor tRNA could be amplified and packaged into infectious HSV-1 virions in the presence of transacting helper virus. The infectious pHE vector has efficient transgene expression in a variety of human cell lines. The designed suppressor tRNA is only about 0.1 kb in size. Thus approximately 15 copies of the tRNA might be packaged into a single 152 kb viral genome. Although we were able to package the suppressor tRNA into the herpes genome, less than 5% of the transduced XP12ROSV cells expressing the mhRGFP demonstrated green fluorescence (FIG. 7). The cellular toxicity and low suppression efficiency is likely secondary to helper virus proteins that shutoff host protein synthesis. Previous studies have demonstrated that the HSV host shutoff genes such as vhs (UL41) and ICP47 (UL54) can inhibit host cell protein synthesis (Kwong, A. D., Kruper, J. A. & Frenkel, N., "Herpes simplex virus host shutoff function", *J Virol* 62, 912–921 (1988); Hardwicke, M. A. & Sandri-Goldin, R. M., "The Herpes simplex virus regulatory protein ICP27 contributes to the decrease in cellular mRNA levels during infection", *J Virol* 68, 4797–4810 (1994)). For example, expression of the vhs gene facilitates the degradation of host mRNA (Kwong, A. D., Kruper, J. A. & Frenkel, N., "Herpes simplex virus host shutoff function", *J Virol* 62, 912–921 (1988). It is possible that these or other helper virus proteins reduced the mRNA stability or expression of the mhRGFP gene and resulted in fewer targets for the suppressor tRNA. Studies are in progress to use the recently developed helper-free packaging system to eliminate the presence of viral host shutoff genes and reduce or eliminate virus cytotoxicity (Fraefel, C. et al., "Helper virus-free transfer of herpes simplex virus type 1 plasmid vectors into neural cells",*J Virol* 70, 7190–7 (1996).

According to the invention, several other human suppressor serine tRNAs have been synthesized and shown to be functional in accordance with the teachings herein. These are disclosed at FIGS. 8–13.

What is claimed is:

1. An oligonucleotide sequence which encodes a synthetic suppressor tRNA consisting of:
   A) a structural gene sequence from a known human tRNA gene, comprising no more than twenty 3' flanking residues and no 5' flanking residues of the human tRNA gene sequence, said sequence comprising an anticodon region for pairing with mRNA;
   B) a total length of less than 150 nucleotides;
   C) and wherein said anticodon region has been modified to recognize a codon different from that which is recognized by the anticodon of the known human tRNA gene.

2. The oligonucleotide of claim 1 wherein said anticodon region has been modified to recognize a stop codon (i.e., UAG, UAA, or UGA).

3. The oligonucleotide of claim 1 further comprising a second oligonucleotide sequence as described in claim 1 wherein said two sequences are in tandem.

4. The oligonucleotide of claim 1 wherein said tRNA structural gene sequence encodes a serine tRNA.

5. The oligonucleotide sequence of claim 1 wherein said tRNA structural gene sequence encodes an arginine tRNA.

6. An oligonucleotid e which encodes a synthetic suppressor tRNA consisting of:
   A) a structural gene sequence from a known human tRNA gene, comprising no more than twenty 3' flanking residues and no 5' flanking residues of the human tRNA gene sequence, said sequence comprising an anticodon region for pairing with mRNA;
   B) a total length of less than 150 nucleotides;
   C) wherein said anticodon sequence has been modified to recognize a codon different from that which is recognized by the anticodon of the known human tRNA gene, wherein said oligonucleotide has a sequence selected from the group consisting of SEQ ID NOS: 1–10, and their complements.

7. A method of restoring translation to a nucleotide sequence which includes a nonsense mutation in a cell comprising: introducing to said cell in vitro a synthetic suppressor tRNA oligonucleotide, said oligonucleotide consisting of
   A) a structural gene sequence from a known human tRNA gene, comprising no more than twenty 3' flanking residues and no 5' flanking residues of the human tRNA gene sequence, said sequence comprising an anticodon region for pairing with mRNA;
   B) a total length of less than 150 nucleotides;
   C) wherein said anticodon region has been modified to recognize a codon different from that which is recognized by the anticodon of the known human tRNA structural gene, wherein said modified anticodon is complementary to said nonsense mutation, such that said synthetic suppressor tRNA oligonucleotide encodes an amino acid which is normally deleted by said nonsense mutation in a nucleotide sequence;
   wherein said synthetic suppressor tRNA oligonucleotide restores translation to said nucleotide sequence, which includes a nonsense mutation.

8. The method of claim 7 wherein said nucleotide sequence with said nonsense mutation is one which has been introduced to said cell.

9. The oligonucleotide of claim 7 wherein said tRNA structural gene sequence encodes a serine tRNA.

10. The oligonucleotide sequence of claim 7 wherein said tRNA structural gene sequence encodes an arginine tRNA.

11. A method of restoring translation to a nucleotide sequence which includes a nonsense mutation in a cell comprising: introducing to said cell in vitro a synthetic suppressor tRNA oligonucleotide, said oligonucleotide consisting of:

A) a structural gene sequence derived from a known human tRNA gene, comprising no more than twenty 3' flanking residues and no 5' flanking residues of the human tRNA gene sequence, said sequence comprising an anticodon region for pairing with mRNA;

B) a total length of less than 150 nucleotides;

C) wherein said anticodon sequence has been modified to recognize a codon different from that which is recognized by the anticodon of the known human tRNA gene, wherein said modified anticodon is complementary to said nonsense mutation, such that said synthetic suppressor tRNA oligonucleotide encodes an amino acid which is normally deleted by said nonsense mutation in a nucleotide sequence, wherein said oligonucleotide has a sequence selected from the group consisting of SEQ ID NOS: 1–10, and their complements; wherein said synthetic suppressor tRNA oligonucleotide restores translation to said nucleotide sequence, which includes a nonsense mutation.

12. A method of restoring translation to a nucleotide sequence which includes a nonsense mutation in a cell comprising: introducing to said cell in vitro a synthetic suppressor tRNA oligonucleotide, said oligonucleotide being one encoded by the sequence of claim 1, wherein said synthetic suppressor tRNA oligonucleotide restores translation to said nucleotide sequence which includes a nonsense mutation.

13. A nucleotide vector comprising the oligonucleotide sequence of claim 1.

14. The nucleotide vector of claim 13 wherein said vector is a viral vector.

15. The vector of claim 13 wherein said vector is a viral vector selected from the group consisting of: a retroviral, adenoviral, adeno-associated, and Herpes simplex viral vector.

16. The method of claim 13 wherein said vector is a Herpes virus vector.

17. The method of claim 13 wherein said vector is a Herpes virus mini amplicon vector comprising:
an Epstein-Barr virus ori P and EBNA-1 sequence to maintain the vector episomally, a hygromycin resistance gene, an HSV-1 lytic replication origin (ori S), and a HSV-1 terminal packaging signal.

18. The vector of claim 13 wherein said vector is the pHhargsup tRNA$^{Opal}$ vector.

19. A transformed host cell comprising the nucleotide sequence of claim 1.

20. A method for introducing a site-specific mutation in a protein containing a nonsense mutation comprising: introducing to a cell in vitro a synthetic suppressor tRNA oligonucleotide, said oligonucleotide consisting of:

A) a structural gene sequence derived from a known human tRNA gene, comprising no more than twenty 3' flanking residues and no 5' flanking residues of the human tRNA gene sequence, said sequence comprising an anticodon region for pairing with mRNA;

B) a total length of less than 150 nucleotides;

C) and wherein said anticodon sequence has been modified to recognize a codon different from that which is recognized by the anticodon of the known human tRNA gene, wherein said anticodon is one which will pair with said nonsense mutation and said tRNA structural gene sequence encodes an amino acid which is deleted by said nonsense mutation; wherein said synthetic suppressor tRNA oligonucleotide introduces a site-specific mutation in a protein containing a nonsense mutation.

21. The methol of claim 20 wherein said tRNA structural gene sequence encodes a serine tRNA.

22. The method sequence of claim 20 wherein said tRNA structural gene sequence encodes an arginine tRNA.

23. A method for introducing a site-specific mutation in a protein containing a nonsense mutation comprising: introducing to a cell in vitro a synthetic suppressor tRNA oligonucleotide, said oligonucleotide consisting of:

A) a structural gene sequence derived from a known human tRNA gene, comprising no more than twenty 3' flanking residues and no 5' flanking residues of the human tRNA gene sequence, said sequence comprising an anticodon region for pairing with mRNA;

B) a total length of less than 150 nucleotides;

C) and wherein said anticodon sequence has been modified to recognize a codon different from that which is recognized by the anticodon of the known human tRNA gene, wherein said anticodon is one which will pair with said nonsense mutation and said tRNA structural gene sequence encodes an amino acid which is deleted by said nonsense mutation, wherein said oligonucleotide has a sequence selected from the group consisting of SEQ ID NOS: 1–10; and their complements; wherein said synthetic suppressor tRNA oligonucleotide introduces a site-specific mutation in a protein containing a nonsense mutation.

24. A method for designing a synthetic suppressor tRNA comprising:

A) identifying a tRNA sequence of interest;

B) identifying the anticodon of said tRNA sequence;

C) designing an alternate anticodon sequence such that a different amino acid is translated in relation to the said anticodon than would normally be;

(D) synthesizing an oligonucleotide comprising:
a) a human tRNA structural gene sequence comprising no more than twenty 3' flanking residues and no 5' flanking residues, said sequence encoding an anticodon region for pairing with mRNA;
b) a total length of less than 150 nucleotides;
c) an anticodon sequence which has been modified to recognize a codon different from that which is originally recognized, wherein said anticodon is one which will pair with a nonsense mutation and said tRNA structural gene sequence encodes an amino acid which is deleted by said nonsense mutation.

25. The method of claim 24 wherein said anticodon region has been modified to recognize a stop codon (i.e., UAG, UAA, or UGA).

26. The method of claim 24 wherein said tRNA structural gene encodes a serine tRNA.

27. The method sequence of claim 24 wherein said tRNA structural gene sequence encodes an arginine tRNA.

28. A method of monitoring transduction of cells comprising: introducing to said cells in vitro an oligonucleotide vector comprising a reporter gene, said reporter gene having been inactivated by introduction of a nonsense mutation; introducing to said cells an oligonucleotide sequence which encodes a suppressor tRNA sequence according to claim 1; assaying for reactivation of the reporter gene, and thereby monitoring the transduction of said cells.

29. The method of claim 28 wherein said reporter gene is selected form the group consisting of: chloramphenicol acetyl transferase and green fluorescent protein.

* * * * *